United States Patent
Algawi et al.

(10) Patent No.: US 11,559,322 B2
(45) Date of Patent: Jan. 24, 2023

(54) MULTI-FUNCTIONAL ENT TOOL

(71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 820 days.

(21) Appl. No.: 16/046,876

(22) Filed: Jul. 26, 2018

(65) Prior Publication Data
US 2019/0038301 A1    Feb. 7, 2019

Related U.S. Application Data

(60) Provisional application No. 62/540,977, filed on Aug. 3, 2017.

(51) Int. Cl.
*A61B 1/233*    (2006.01)
*A61B 1/05*    (2006.01)
(Continued)

(52) U.S. Cl.
CPC .......... *A61B 17/24* (2013.01); *A61B 1/00096* (2013.01); *A61B 1/018* (2013.01);
(Continued)

(58) Field of Classification Search
CPC ........ A61B 1/00133; A61M 25/09041; A61M 25/0113
See application file for complete search history.

(56) References Cited

U.S. PATENT DOCUMENTS 5,634,475 A    6/1997 Wolvek
6,929,600 B2 *    8/2005 Hill .................... A61B 1/00052
600/120
(Continued)

FOREIGN PATENT DOCUMENTS

WO    WO 2008/049088 A2    4/2008

OTHER PUBLICATIONS

Partial European Search Report and Written Opinion dated Oct. 9, 2018, for Application No. 18186998.3, 14 pages.
(Continued)

*Primary Examiner* — Matthew J Kasztejna
(74) *Attorney, Agent, or Firm* — Frost Brown Todd LLP

(57) ABSTRACT

An ENT tool has a tool chassis having a chassis channel and a tool chassis distal end. A tubular probe is dimensioned to be inserted into a human patient orifice, the probe is rotatable about a probe axis of symmetry, and the probe has a probe proximal end rotatingly connected to the tool chassis distal end. A balloon insertion mechanism is slidingly located within the chassis channel, and is configured to fixedly accept a balloon sinuplasty mechanism penetrating the tubular probe. A guidewire adjustment section is fixedly attached to the balloon insertion mechanism, and the section has a rotatable enclosure. A plurality of rollers are disposed within the enclosure and are configured so that on rotation of the enclosure the rollers grip and rotate a guidewire positioned between the rollers, and, absent rotation of the enclosure, release the guidewire and permit distal and proximal translation of the guidewire.

20 Claims, 23 Drawing Sheets

(51) Int. Cl.
*A61B 1/227* (2006.01)
*A61B 17/24* (2006.01)
*A61B 1/00* (2006.01)
*A61B 1/018* (2006.01)
*A61B 34/20* (2016.01)
*A61B 5/06* (2006.01)
*A61B 1/267* (2006.01)
*A61M 25/09* (2006.01)
*A61B 1/07* (2006.01)
*A61B 17/00* (2006.01)
*A61M 29/02* (2006.01)
*A61B 1/12* (2006.01)
*A61B 90/00* (2016.01)

(52) U.S. Cl.
CPC ............... *A61B 1/05* (2013.01); *A61B 1/227* (2013.01); *A61B 1/233* (2013.01); *A61B 1/267* (2013.01); *A61B 5/062* (2013.01); *A61B 34/20* (2016.02); *A61M 25/09041* (2013.01); *A61B 1/0014* (2013.01); *A61B 1/00133* (2013.01); *A61B 1/07* (2013.01); *A61B 1/126* (2013.01); *A61B 90/361* (2016.02); *A61B 2017/0034* (2013.01); *A61B 2017/00557* (2013.01); *A61B 2034/2051* (2016.02); *A61B 2034/2072* (2016.02); *A61B 2217/005* (2013.01); *A61M 29/02* (2013.01); *A61M 2025/09008* (2013.01); *A61M 2025/09125* (2013.01); *A61M 2029/025* (2013.01); *A61M 2210/0681* (2013.01)

(56) References Cited

U.S. PATENT DOCUMENTS

| 10,820,923 | B2 | 11/2020 | Govari |
| 11,027,105 | B2 | 6/2021 | Matlock et al. |
| 2007/0112358 | A1 | 5/2007 | Abbott et al. |
| 2007/0219550 | A1 | 9/2007 | Thompson et al. |
| 2007/0293726 | A1 | 12/2007 | Goldfarb et al. |
| 2008/0236575 | A1* | 10/2008 | Chuda ............ A61B 1/05 128/200.26 |
| 2009/0082722 | A1* | 3/2009 | Munger ............ A61M 25/0113 604/95.01 |
| 2009/0105645 | A1* | 4/2009 | Kidd ............... A61M 25/0133 604/108 |
| 2010/0099946 | A1 | 4/2010 | Jenkins et al. |
| 2012/0071856 | A1 | 3/2012 | Goldfarb et al. |
| 2012/0071857 | A1* | 3/2012 | Goldfarb ......... A61M 25/09041 604/514 |
| 2014/0277043 | A1 | 9/2014 | Jenkins et al. |
| 2015/0202414 | A1* | 7/2015 | Hwang ............ A61B 5/150389 600/585 |
| 2016/0082233 | A1* | 3/2016 | Ha ............. A61M 29/02 606/199 |
| 2016/0287065 | A1* | 10/2016 | Ha ............. A61B 1/00133 |
| 2017/0065396 | A1* | 3/2017 | Look ............ A61B 17/320758 |
| 2018/0110968 | A1* | 4/2018 | Ngo-Chu ............ A61M 29/02 |
| 2018/0303505 | A1* | 10/2018 | Algawi ............ A61M 29/02 |

OTHER PUBLICATIONS

European Search Report and Written Opinion dated Feb. 8, 2019, for Application No. 18186998.3, 13 pages.

* cited by examiner

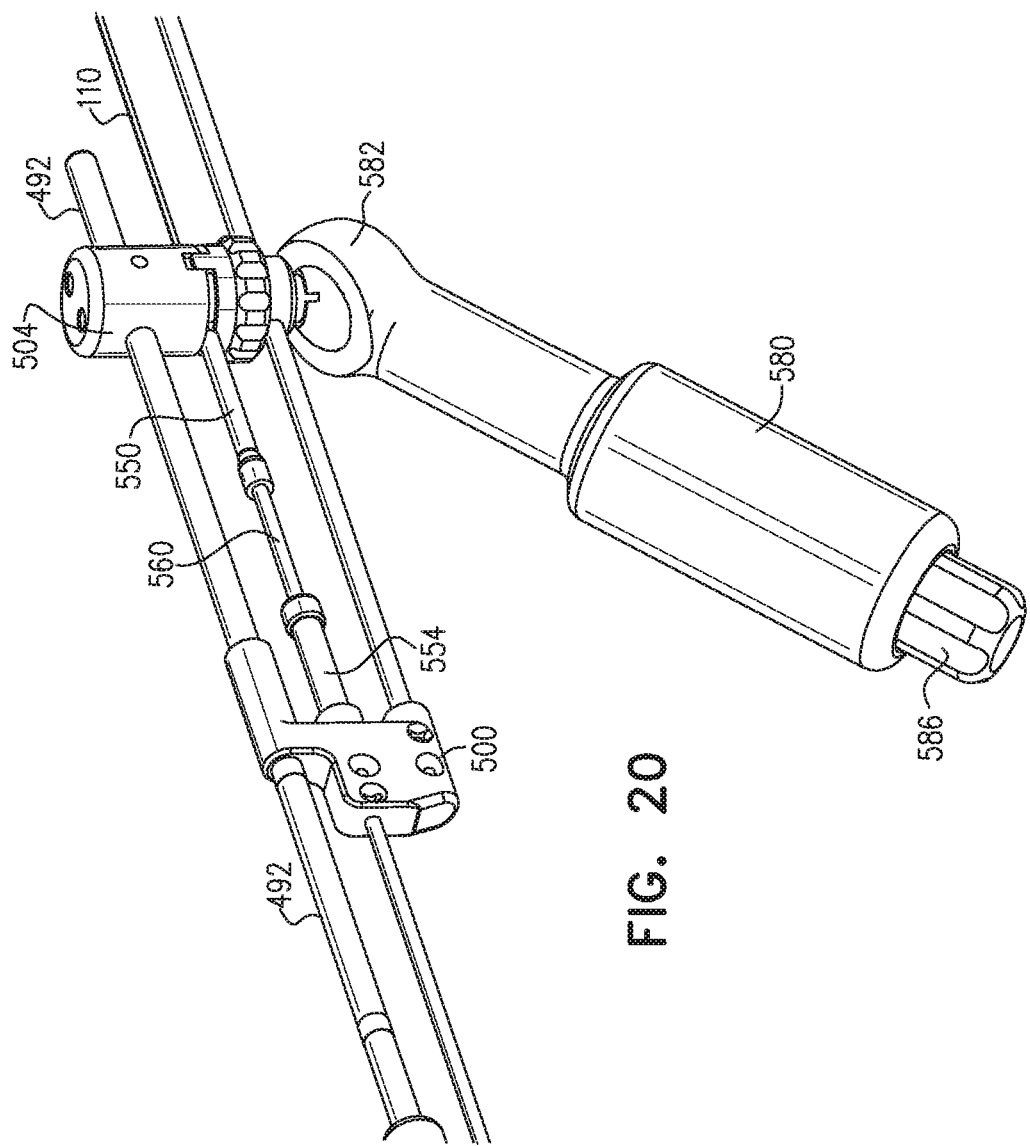

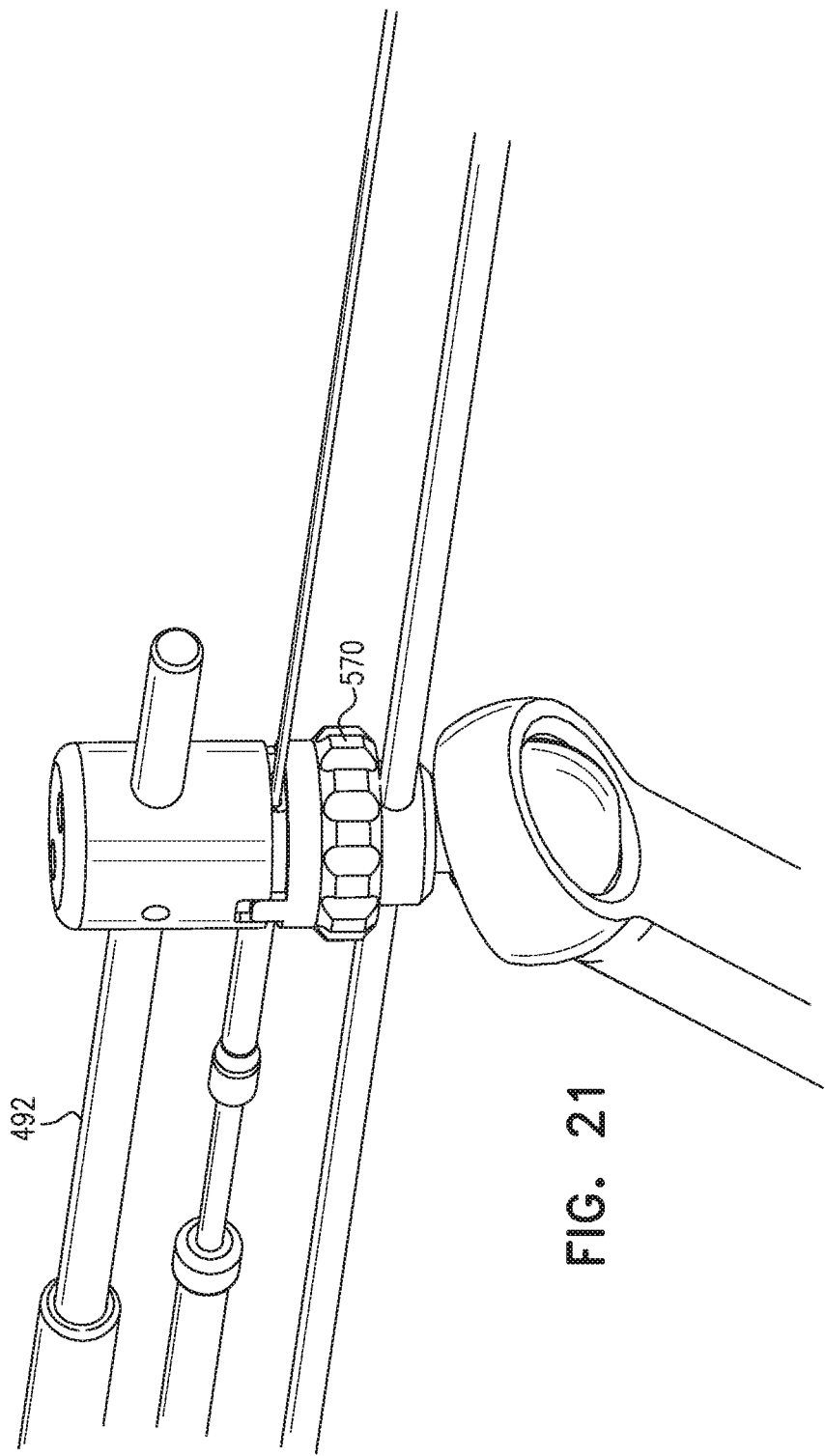

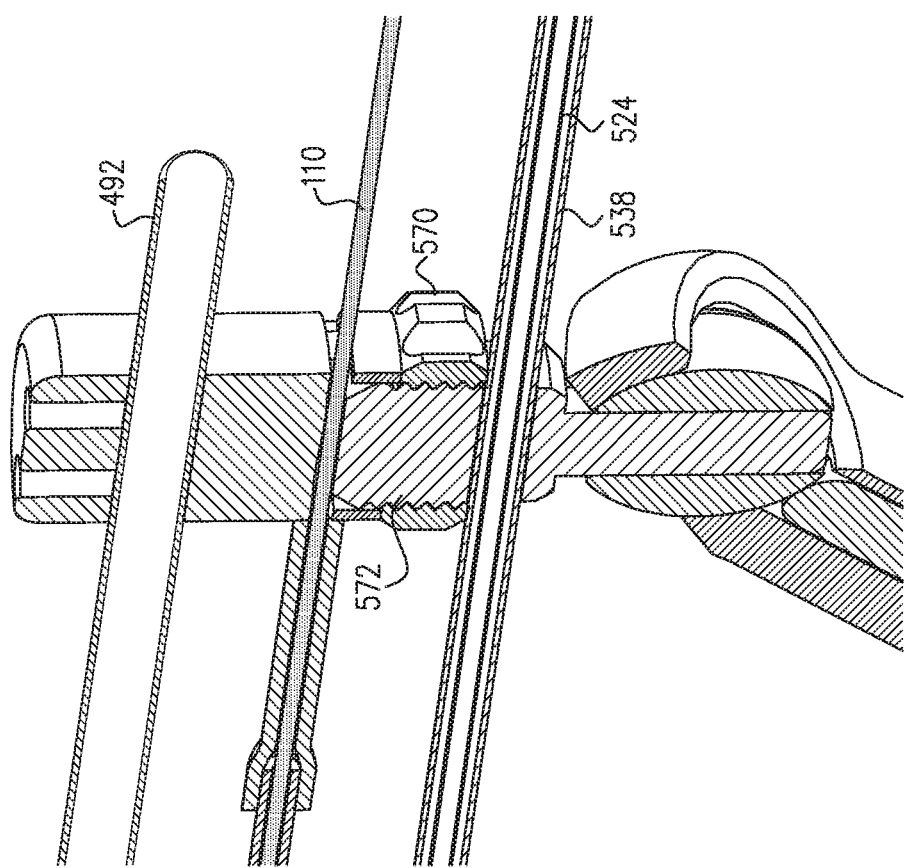

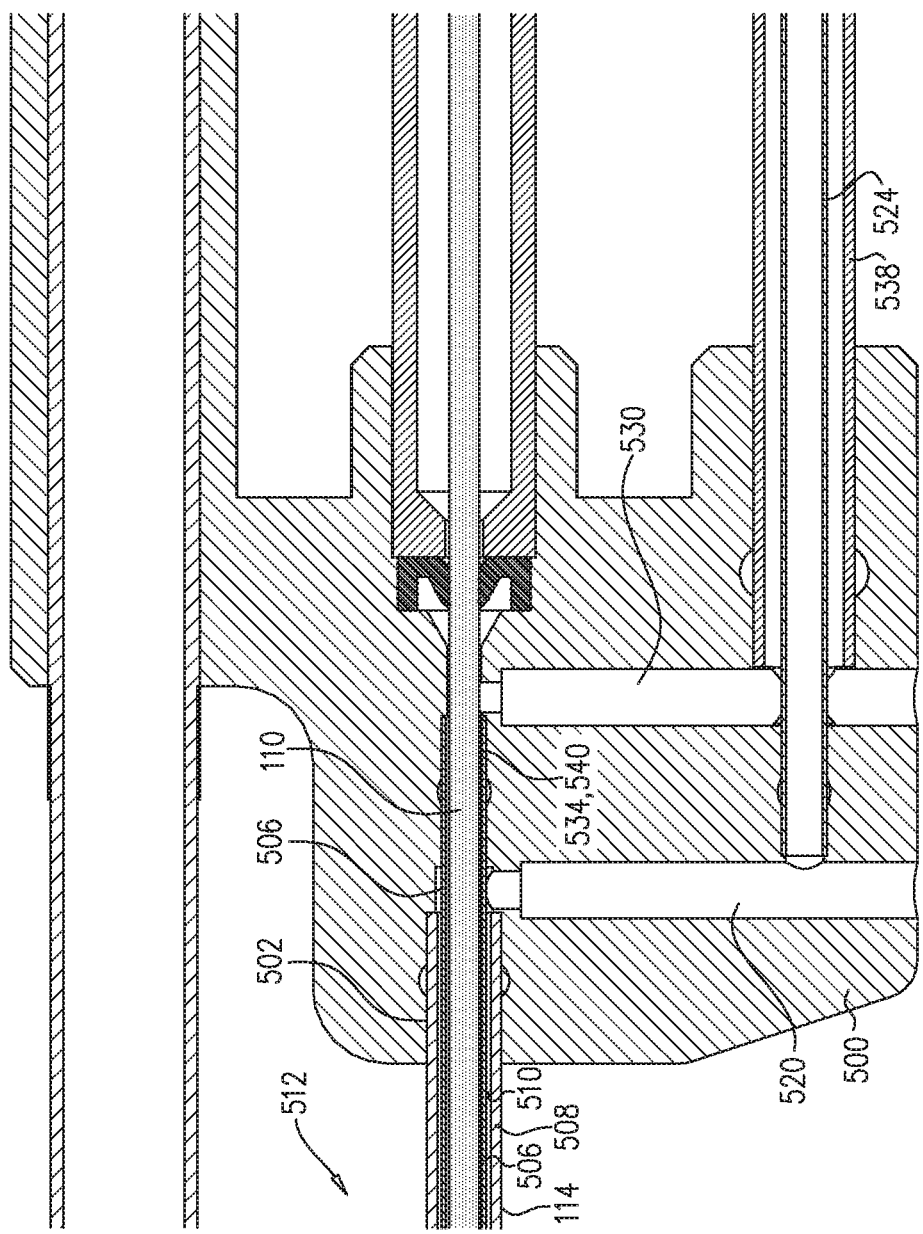

MULTI-FUNCTIONAL ENT TOOL

CROSS-REFERENCE TO RELATED APPLICATION

This application claims the benefit of U.S. Provisional Patent Application 62/540,977, filed 3 Aug. 2017, which is incorporated herein by reference.

FIELD OF THE INVENTION

This invention relates generally to surgical tools, and specifically to a surgical tool used for ENT (ear, nose, and throat) procedures.

BACKGROUND OF THE INVENTION

An ENT procedure typically has to cope with a number of constraints which limit the flexibility of a physician performing the procedure. I.e., there is limited access to the area being operated on, the region being operated on is typically a relatively complicated structure, and in addition may be close to critical organs of the body such as the optic nerves. Some existing tools for ENT procedures are described below.

U.S. Patent Application 2014/0277043, issued as U.S. Pat. No. 9,629,684 on Apr. 25, 2017, to Jenkins et al. describes an apparatus for treatment of ethmoid sinusitis. The apparatus may be used to form an opening in a sinus wall, and comprises a first cutting member and a second cutting member. The first cutting member comprises a helical blade.

U.S. Patent Application 2007/0219550, now abandoned, to Thompson et al. describes a device for dissecting tissue and/or guidance of a second device to a desired physiological location. The device has an elongate shaft comprising a proximal portion and a distal portion, and the distal portion has a plurality of segments that articulate with respect to one another.

U.S. Patent Application 2010/0099946, issued as U.S. Pat. No. 8,414,473 on Apr. 9, 2013, to Jenkins et al. describes a device for dilating an ostium of a paranasal sinus of a human or animal subject. The device may include a handle, an elongate shaft having a proximal end coupled with the handle and extending to a distal end, and a guidewire disposed through at least a portion of the shaft lumen.

U.S. Patent Application 2007/0112358 to Abbott et al., now abandoned, describes a system for treating a septal defect having an implantable treatment apparatus. The application also describes devices for controlling delivery of the treatment apparatus.

SUMMARY OF THE INVENTION

An embodiment of the present invention provides an ear, nose, and throat (ENT) tool, including:

a tool chassis having a chassis channel and a tool chassis distal end;

a tubular probe dimensioned to be inserted into an orifice of a human patient, the probe being rotatable about a probe axis of symmetry, and having a probe proximal end rotatingly connected to the tool chassis distal end;

a balloon insertion mechanism, slidingly located within the chassis channel, configured to fixedly accept a balloon sinuplasty mechanism penetrating the tubular probe;

a guidewire adjustment section fixedly attached to the balloon insertion mechanism, the section having a rotatable enclosure; and a plurality of rollers disposed within the enclosure and configured so that on rotation of the enclosure the rollers grip and rotate a guidewire positioned between the rollers, and, absent rotation of the enclosure, release the guidewire and permit distal and proximal translation of the guidewire.

In a disclosed embodiment the tool chassis distal end consists of a joint connected to the probe proximal end, the joint enabling rotation of the tubular probe about an axis orthogonal to the probe axis of symmetry.

In another disclosed embodiment the balloon insertion mechanism includes one or more gearwheels configured to engage the guidewire on application of pressure to the one or more gearwheels, and to disengage the guidewire on removal of the pressure, and configured, on application of the pressure, to translate the guidewire distally and proximally on rotation of the one or more gearwheels.

In a further disclosed embodiment the rotatable enclosure consists of an equilateral curvilinear triangular right prism enclosure, and the plurality of rollers are three rollers disposed within the enclosure.

In a yet further disclosed embodiment a camera is fixedly installed in a distal tip of the tubular probe. Typically, there are one or more illumination channels in the distal tip providing light for the camera. In some embodiments there are, in the distal tip, one or more fluid channels and deflectors configured to convey fluid that traverses faces of the camera and the illumination channels.

There is further provided, according to an embodiment of the present invention, an ear, nose, and throat (ENT) tool, including:

a tool chassis having a chassis channel and a tool chassis distal end;

a tubular probe dimensioned to be inserted into an orifice of a human patient, the probe being rotatable about a probe axis of symmetry, and having a probe proximal end rotatingly connected to the tool chassis distal end;

a balloon insertion mechanism, slidingly located within the chassis channel, configured to fixedly accept a balloon sinuplasty mechanism penetrating the tubular probe;

a couple, having a couple length, connected to the balloon insertion mechanism;

a guidewire adjustment section, slidingly located within the chassis channel, connected by the couple to the balloon insertion mechanism so as to be movable therefrom by a predetermined distance responsive to the couple length; and a compressible tubular structure retained within the section, the structure having a central lumen configured to enclose a guidewire, the structure being configured on application of pressure to grip the guidewire, and, absent the pressure, to release the guidewire and permit distal and proximal translation of the guidewire relative to the structure.

The tubular structure may be rotatable about the central lumen.

There is further provided, according to an embodiment of the present invention, an ear, nose, and throat (ENT) tool, including:

a suction tube having a central lumen configured to apply suction to a human patient;

a connector having a central passage, the connector being coupled to the suction tube so that the central lumen connects to the central passage;

a tubular probe having a probe lumen, the probe being dimensioned to be inserted into an orifice of the human patient, the probe being rotatable about a probe axis of symmetry, and having a probe proximal end connected to the connector so that the probe lumen connects to the central passage; and a balloon sinuplasty mechanism holder having a mechanism hole penetrated by the suction tube so that the holder is slidingly held by the tube acting as a retaining rail for the holder, the balloon sinuplasty mechanism holder being configured to fixedly accept a balloon sinuplasty mechanism penetrating the tubular probe and a guidewire directed through the balloon sinuplasty mechanism.

In an embodiment the ENT tool has a lock having a lock hole penetrated by the suction tube so that the lock is slidingly held by the tube, the lock being coupled to the balloon sinuplasty mechanism holder so that in a locked state of the lock the holder is fixed to the tube and the guidewire is fixed with respect to the holder, and in an unlocked state of the lock the holder is free to move on the tube and the guidewire is free to move with respect to the holder.

A handle for the tool may be connected to the lock.

There is further provided, according to an embodiment of the present invention, a method, including:

providing an ENT (ear, nose, and throat) tool chassis having a chassis channel and a tool chassis distal end;

dimensioning a tubular probe, having a probe proximal end, to be inserted into an orifice of a human patient, the probe being rotatable about a probe axis of symmetry;

rotatingly connecting the probe proximal end to the tool chassis distal end;

slidingly locating a balloon insertion mechanism within the chassis channel;

configuring the balloon insertion mechanism to fixedly accept a balloon sinuplasty mechanism penetrating the tubular probe;

fixedly attaching a guidewire adjustment section to the balloon insertion mechanism, the section having a rotatable enclosure;

disposing a plurality of rollers within the enclosure; and configuring the rollers so that on rotation of the enclosure the rollers grip and rotate a guidewire positioned between the rollers, and, absent rotation of the enclosure, release the guidewire and permit distal and proximal translation of the guidewire.

There is further provided, according to an embodiment of the present invention, a method, including:

providing an ENT (ear, nose, and throat) tool chassis having a chassis channel and a tool chassis distal end;

dimensioning a tubular probe to be inserted into an orifice of a human patient, the probe being rotatable about a probe axis of symmetry and having a probe proximal end;

rotatingly connecting the probe proximal end to the tool chassis distal end;

slidingly locating a balloon insertion mechanism within the chassis channel, the mechanism being configured to fixedly accept a balloon sinuplasty mechanism penetrating the tubular probe;

connecting a couple, having a couple length, to the balloon insertion mechanism;

slidingly locating a guidewire adjustment section within the chassis channel;

connecting the guidewire adjustment section by the couple to the balloon insertion mechanism so that the section and mechanism are movable therebetween by a predetermined distance responsive to the couple length; and retaining a compressible tubular structure within the section, the structure having a central lumen configured to enclose a guidewire, the structure being configured on application of pressure to grip the guidewire, and, absent the pressure, to release the guidewire and permit distal and proximal translation of the guidewire relative to the structure.

There is further provided, according to an embodiment of the present invention, a method, including:

providing a suction tube having a central lumen configured to apply suction to a human patient;

coupling a connector having a central passage to the suction tube so that the central lumen connects to the central passage;

dimensioning a tubular probe, having a probe lumen and a probe proximal end, to be inserted into an orifice of the human patient, the probe being rotatable about a probe axis of symmetry;

connecting the probe proximal end to the connector so that the probe lumen connects to the central passage;

providing a balloon sinuplasty mechanism holder having a mechanism hole, the balloon sinuplasty mechanism holder being configured to fixedly accept a balloon sinuplasty mechanism penetrating the tubular probe and a guidewire directed through the balloon sinuplasty mechanism; and inserting the suction tube into the mechanism hole so that the holder is slidingly held by the tube acting as a retaining rail for the holder.

The present disclosure will be more fully understood from the following detailed description of the embodiments thereof, taken together with the drawings, in which:

BRIEF DESCRIPTION OF THE DRAWINGS

FIGS. 19-23 are schematic diagrams of a multifunctional ENT tool, according to a further alternative embodiment of the present invention.

DETAILED DESCRIPTION OF EMBODIMENTS

Overview

Embodiments of the present invention provide a physician performing an ENT (ear nose and throat) procedure with a single balloon sinuplasty tool that has a multiplicity of functions. The tool is designed to be held by one hand of the physician, and the physician is able to activate the multiple functions with his/her hand.

The tool functions include:
Multiple deflections of the tool's distal end
A guidewire insertion mechanism
A balloon insertion mechanism
A camera and illumination at the tools' distal tip
An adjustable handle In addition to the functions listed above, the tool provides channels for suction from the distal end, for inflation of the balloon, and for irrigation at the distal end.

By incorporating all the above functions into one tool, and by enabling the majority of the functions to be implemented by the one hand holding the tool, the physician performing the procedure has substantially more freedom of movement than in prior art systems.

Thus, an embodiment of the present invention provides an ENT tool comprising a tool chassis having a chassis channel and a tool chassis distal end. A tubular probe that is dimensioned to be inserted into an orifice of a human patient, the probe being rotatable about a probe axis of symmetry and having a probe proximal end, is rotatingly connected to the tool chassis distal end.

A balloon insertion mechanism is slidingly located within the chassis channel, and is configured to fixedly accept a balloon sinuplasty mechanism penetrating the tubular probe. There is also a guidewire adjustment section that is fixedly attached to the balloon insertion mechanism, and the section has a rotatable enclosure.

A plurality of rollers are disposed within the enclosure and are configured so that on rotation of the enclosure the rollers grip and rotate a guidewire positioned between the rollers. In addition, absent rotation of the enclosure, the rollers release the guidewire and permit distal and proximal translation of the guidewire.

DETAILED DESCRIPTION

Figure 1:
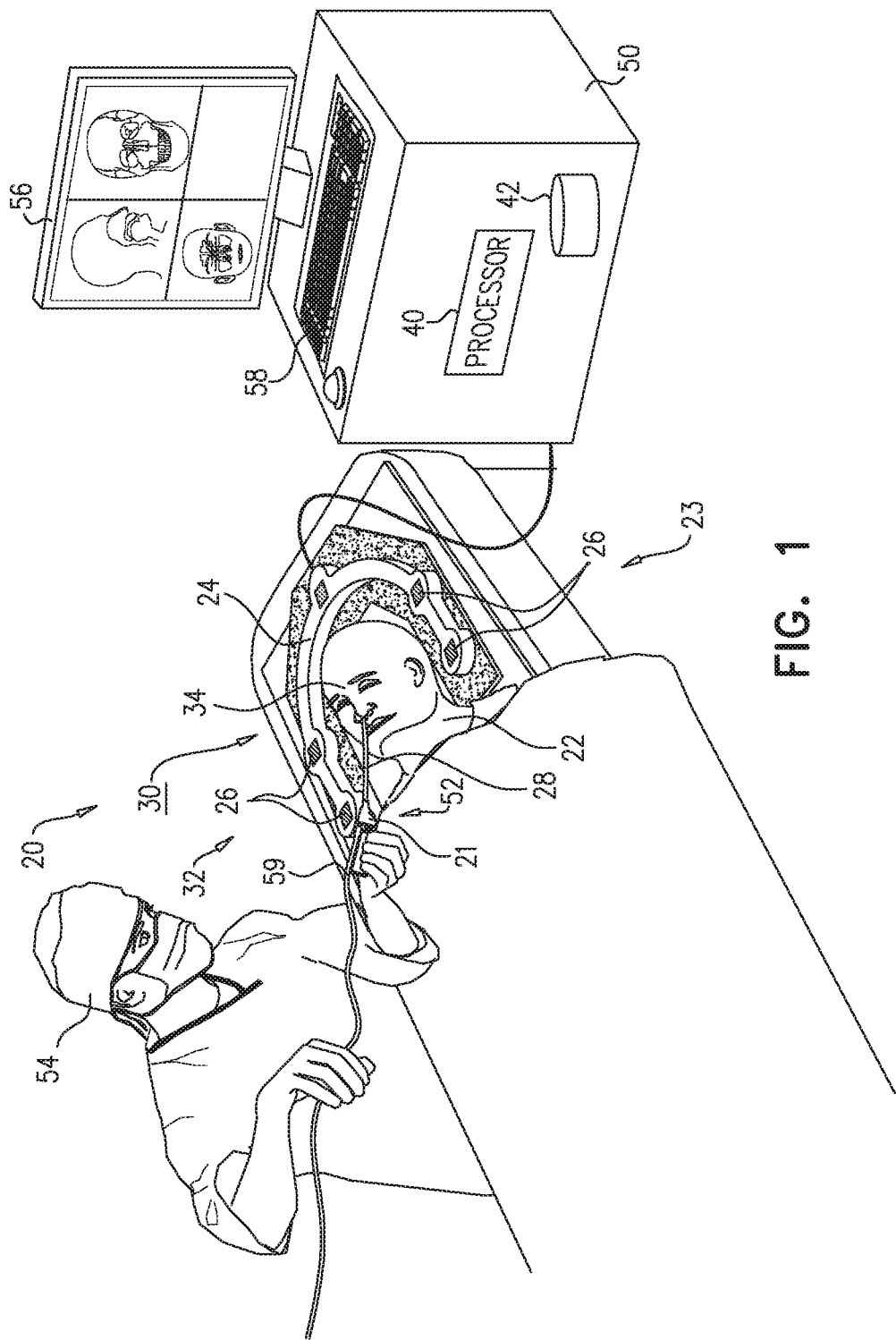
FIG. 1 is a schematic illustration of an ENT (ear, nose, and throat) system, according to an embodiment of the present invention.

Reference is now made to FIG. 1, which is a schematic illustration of an ENT (ear, nose, and throat) system 20, according to an embodiment of the present invention. In the following description a multifunctional ENT tool 21 in system 20 is assumed to be used to perform a balloon sinuplasty procedure on a patient 22, although it will be understood that the tool may be used to perform other procedures on the patient.

Tool 21 comprises one or more magnetic sensors 32, typically single axis coils or a triple axis coils, that are tracked during the procedure by a magnetic tracking system 23. For the tracking to be effective, in system 20 frames of reference of a CT (computerized tomography) image of patient 22 and of magnetic tracking system 23, are registered. While the CT image may typically comprise a magnetic resonance imaging (MRI) image or a fluoroscopic image, in the description herein the image is assumed to comprise, by way of example, a fluoroscopic CT image.

Prior to and during the sinus procedure, a magnetic radiator assembly 24, comprised in the magnetic tracking system, is positioned beneath the patient's head. Assembly 24 comprises magnetic field radiators 26 which are fixed in position and which transmit alternating magnetic fields into a region 30 wherein the head of patient 22 is located. Potentials generated by a magnetic sensor such as sensor 32 in region 30, in response to the magnetic fields, enable the position and the orientation of the sensor to be measured in the magnetic tracking system's frame of reference.

By way of example, radiators 26 of assembly 24 are arranged in an approximately horseshoe shape around the head of patient 22. However, alternate configurations for the radiators of assembly 24 will be apparent to those having skill in the art, and all such configurations are assumed to be comprised within the scope of the present invention.

Prior to the procedure, the registration of the frames of reference of the magnetic tracking system with the CT image may be performed by positioning a magnetic sensor at known positions, such as the tip of the patient's nose, of the image. However, any other convenient system for registration of the frames of reference may be used.

Elements of system 20, including radiators 26 and sensors 32, are under overall control of a system processor 40. Processor 40 may be mounted in a console 50, which comprises operating controls 58 that typically include a keypad and/or a pointing device such as a mouse or trackball. Console 50 connects to the radiators and to sensors 32 via one or more cables cable and/or wirelessly. Physician 54 uses operating controls 58 to interact with the processor while performing the ENT procedure using system 20. While performing the procedure, the processor may present results of the procedure on a screen 56.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Figure 2:
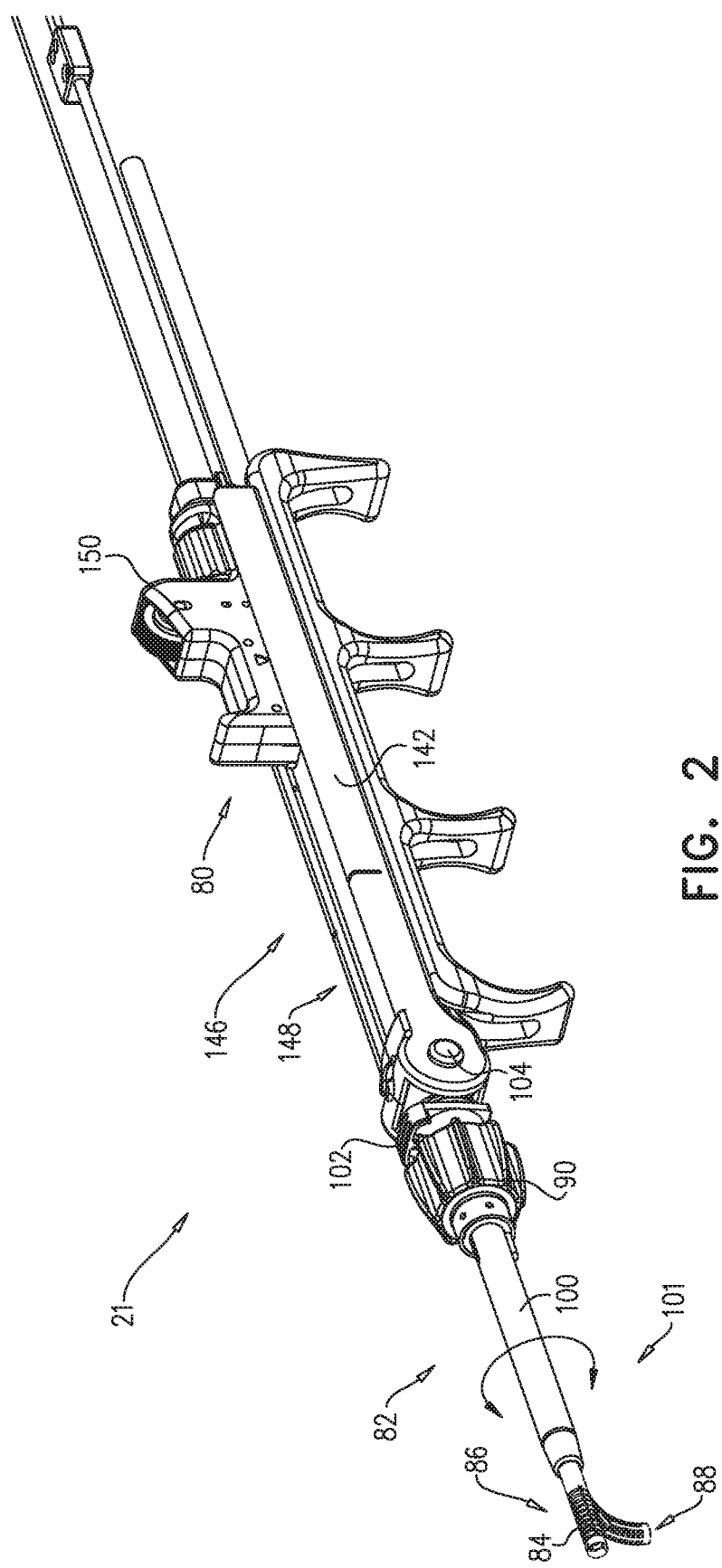
FIG. 2 is a schematic diagram of a tool used in the system in a first configuration, according to an embodiment of the present invention.
Figure 3:
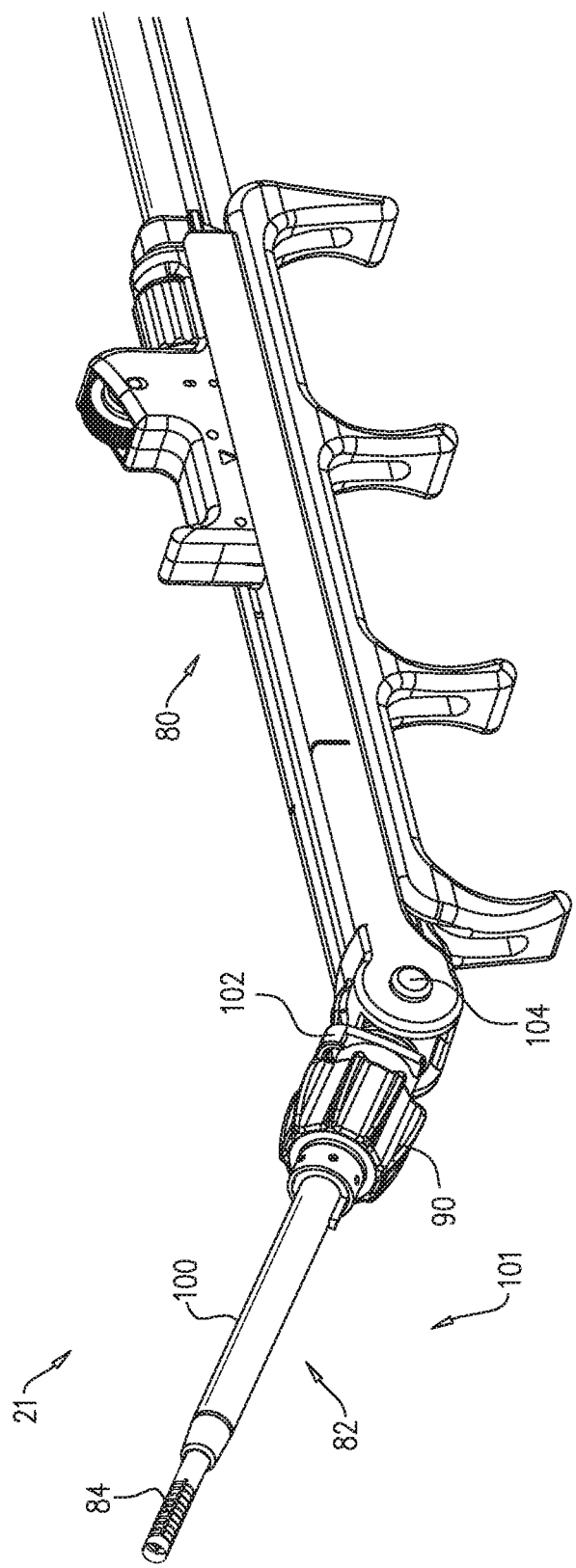
FIG. 3 is a schematic diagram of the tool in a second configuration, according to an embodiment of the present invention.
Figure 4:
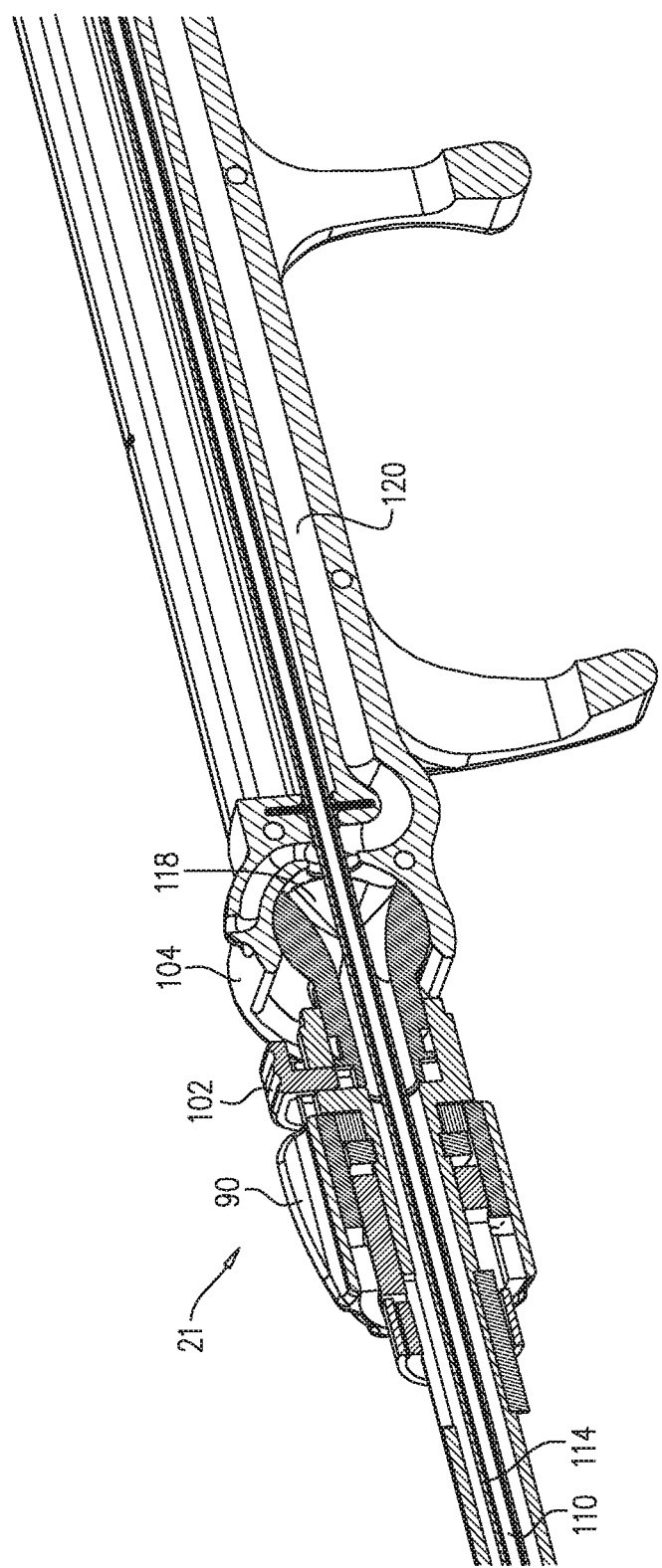
FIG. 4 is a schematic sectional view of a portion of the tool, according to an embodiment of the present invention.

FIG. 2 is a schematic diagram of tool 21 in a first configuration, FIG. 3 is a schematic diagram of the tool in a second configuration, and FIG. 4 is a schematic sectional view of a portion of the tool, according to an embodiment of the present invention. Tool 21 comprises a proximal section 80 and a distal section 82 which are connected together, but the distal section may be disassembled and removed from the proximal section.

At its distal end distal section 82 comprises an articulated tubular section 84, which may be adjustably bent from a straight configuration 86 to a curved configuration 88, the latter being schematically shown in the diagram by broken lines. The adjustment from the straight to the bent configuration, and vice versa, may be performed by clockwise and counter-clockwise rotation of a knob 90. U.S. patent application Ser. No. 15/155,850, filed May 16, 2016, issued as U.S. Pat. No. 10,820,923 on Nov. 3, 2020, titled "Insertion Tube with Deflectable Tip," which is incorporated herein by reference, describes the construction and operation of such a deflectable articulated section.

Tubular section 84 is fixedly connected at its proximal end to a tube 100 which may be rotated about its axis of symmetry, as indicated by the double headed arrow in the figure. The rotation of tube 100 may be implemented by rotating knob 90. Knob 90 thus performs two functions: bending of articulated section 84, and rotation of tube 100. Which function is performed is according to the position of a sliding control 102. In a first position of the control rotation of knob 90 causes articulated section 84 to deflect, while tube 100 is stationary. In a second position of the control rotation of the knob causes tube 100 to rotate, with the knob about the tube axis of symmetry, while section 84 remains in its deflected (or undeflected) state.

Tube 100 and section 84 together form a tubular probe 101, and the probe is dimensioned to be insertable into an orifice of patient 22, such as a nostril and/or a sinus of the patient.

Distal section 82 is also able to rotate with respect to proximal section 80, about an axis orthogonal to the axis of symmetry of tube 100, since the proximal and distal sections of the tool are connected by a joint 104. Joint 104 is configured to allow the distal section to rotate to a number of preselected angles with respect to the proximal section, on compression and release of the joint, typically by the physician's thumb and finger. FIG. 3 illustrates distal section 82 rotated with respect to proximal section 80.

Tube 100 and articulated section 84 comprise central lumens which permit the passage of a guidewire 110 and a balloon sinuplasty mechanism 114, from proximal section 80, through the lumens. The guidewire and mechanism are illustrated in FIG. 4, and their operation and construction are described in more detail below. As is also described below, there is a channel in balloon sinuplasty mechanism 114 for air to inflate the balloon of the mechanism, and there is also a channel between the mechanism and the guidewire permitting irrigation fluid to be transferred to the distal end of distal section 82. The air and irrigation fluid channels of mechanism 114 are more clearly seen in FIG. 23, and are described in more detail below. Within joint 104 there is a flexible seal 118, which permits the sinuplasty mechanism to traverse the joint, but prevents fluid from returning back into proximal section 80.

In addition to the air and fluid channels referred to above, tool 21 also comprises a suction channel 120, which traverses proximal section 80 and joint 104 in its various positions, so that suction may be applied to the lumen of tube 100.

Figure 5:
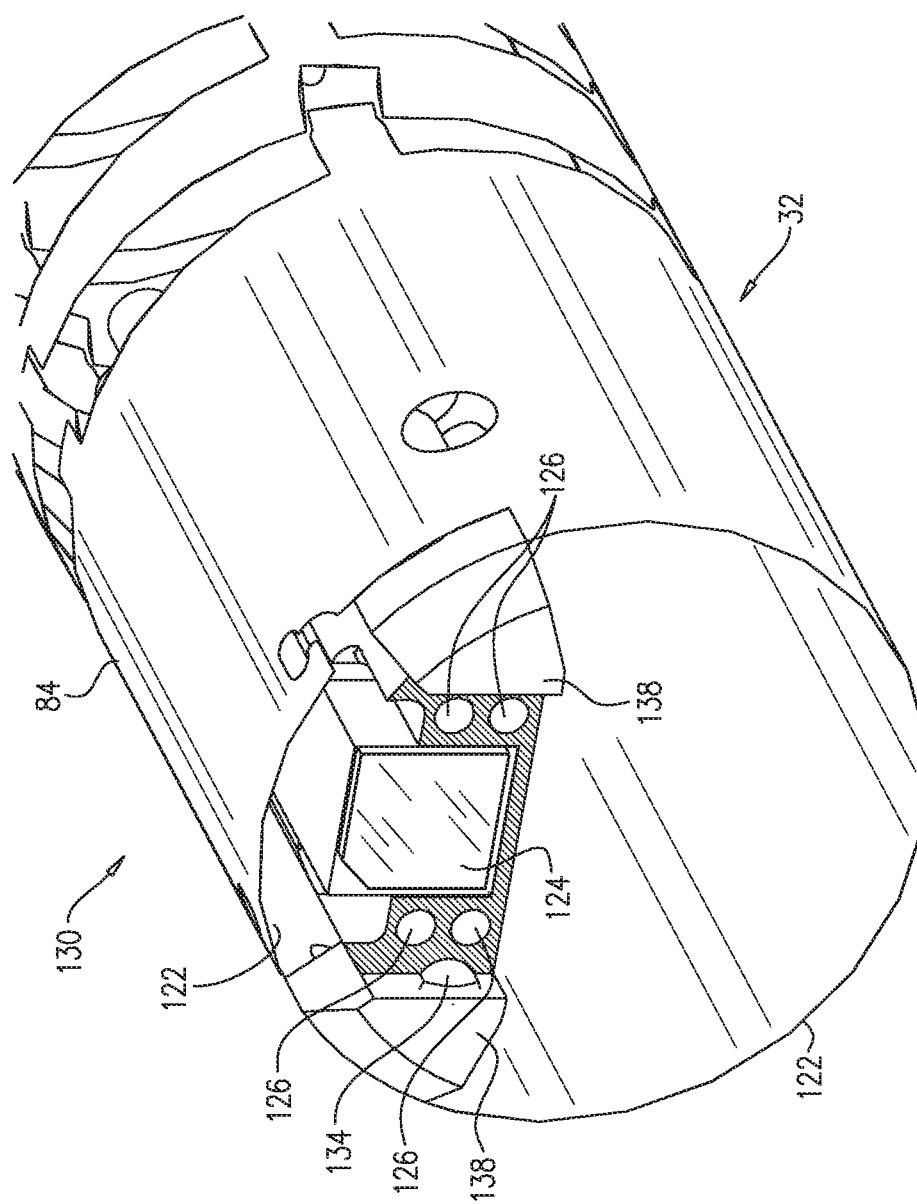
FIG. 5 is a schematic diagram of a distal tip of an articulated section of the tool, according to an embodiment of the present invention.
Figure 6:
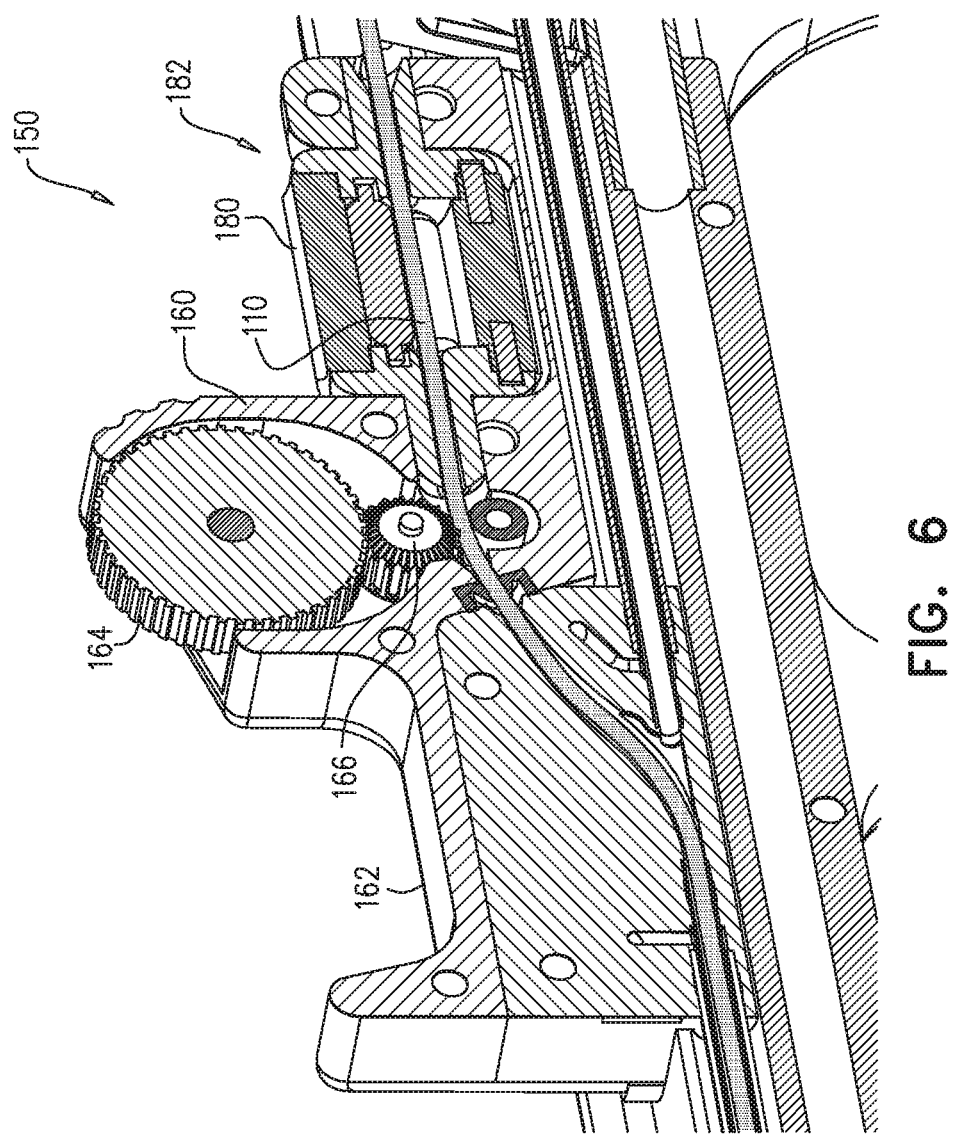
FIGS. 6-10 are schematic diagrams of a guidewire and a balloon insertion mechanism, according to an embodiment of the present invention.
Figure 7:
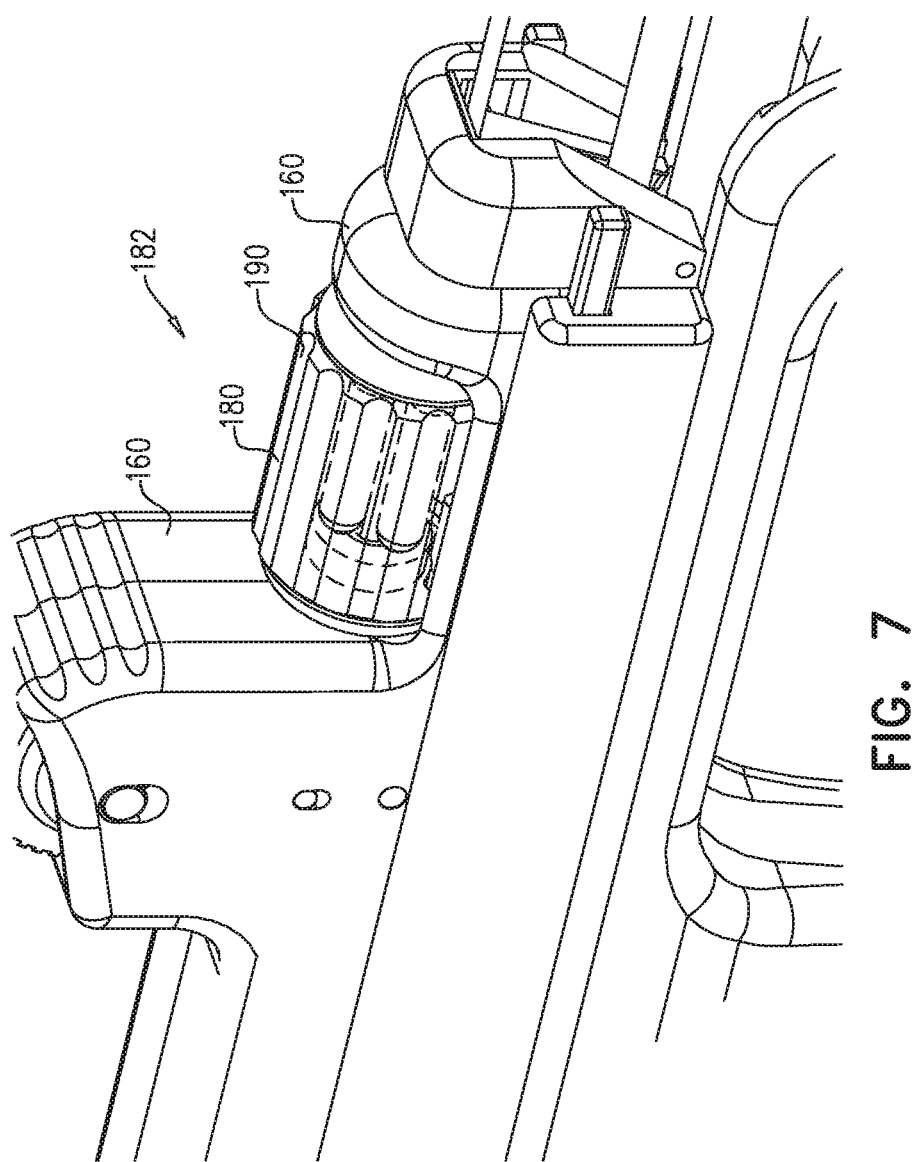
Figure 8:
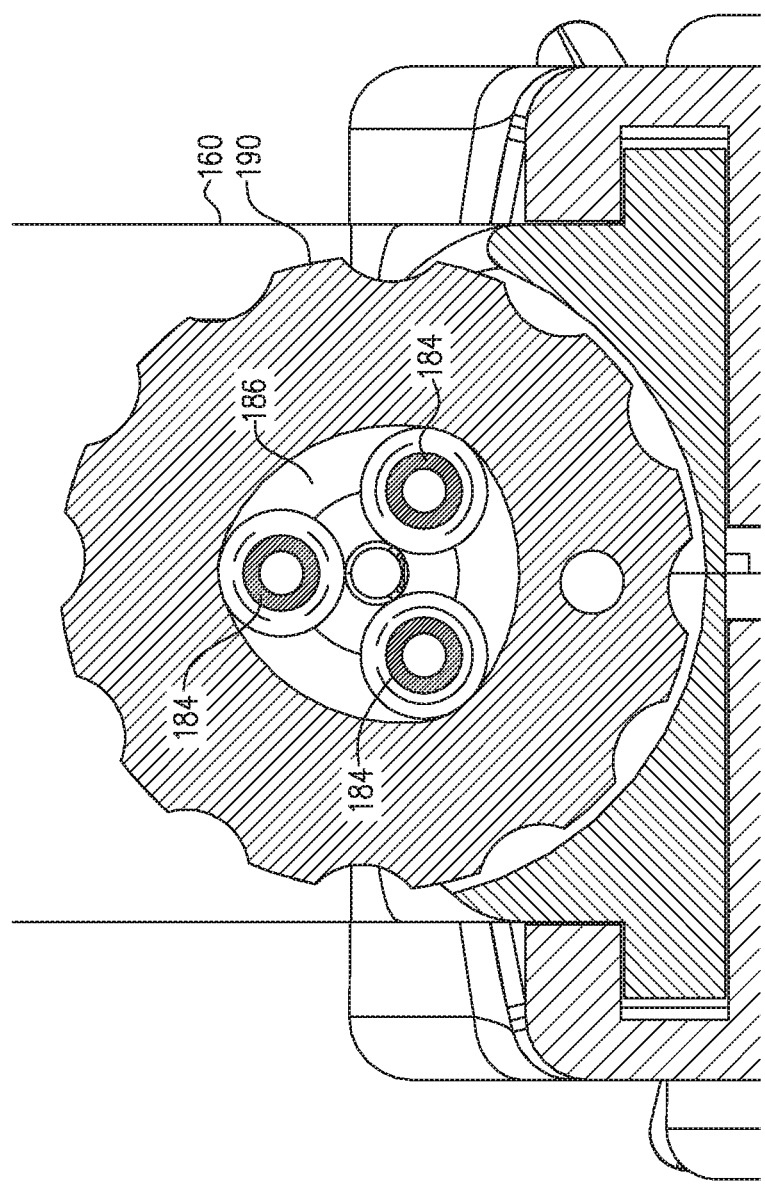
Figure 9:
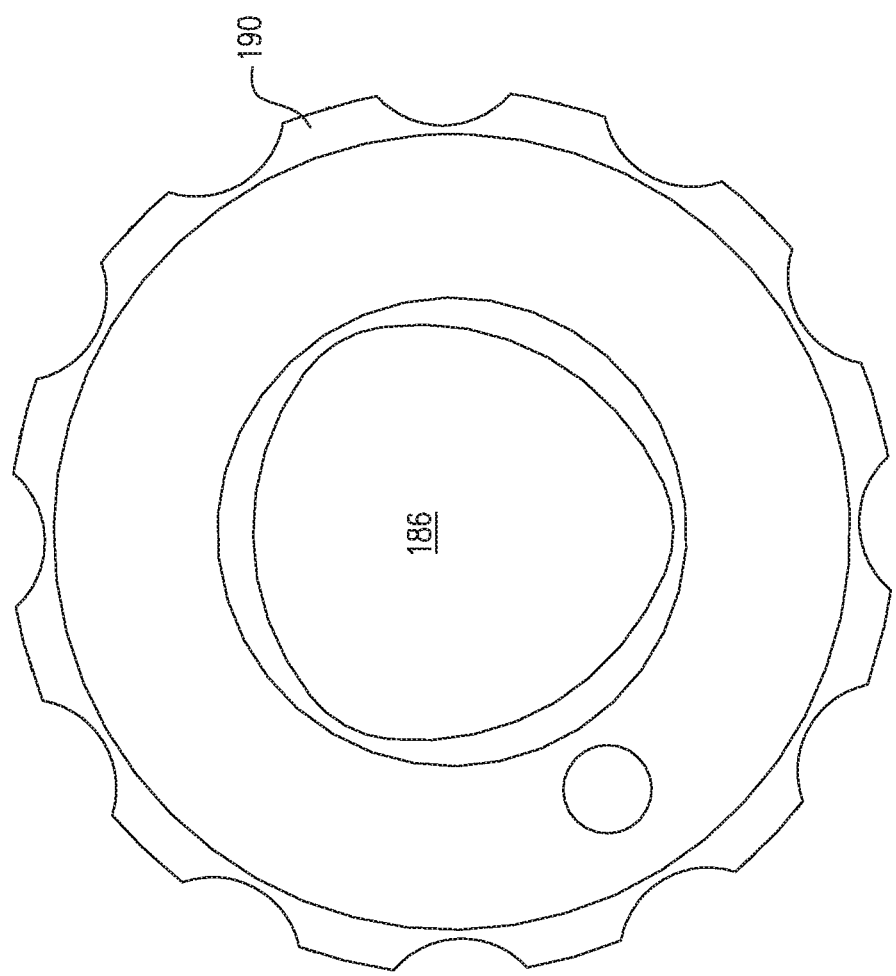
Figure 10:
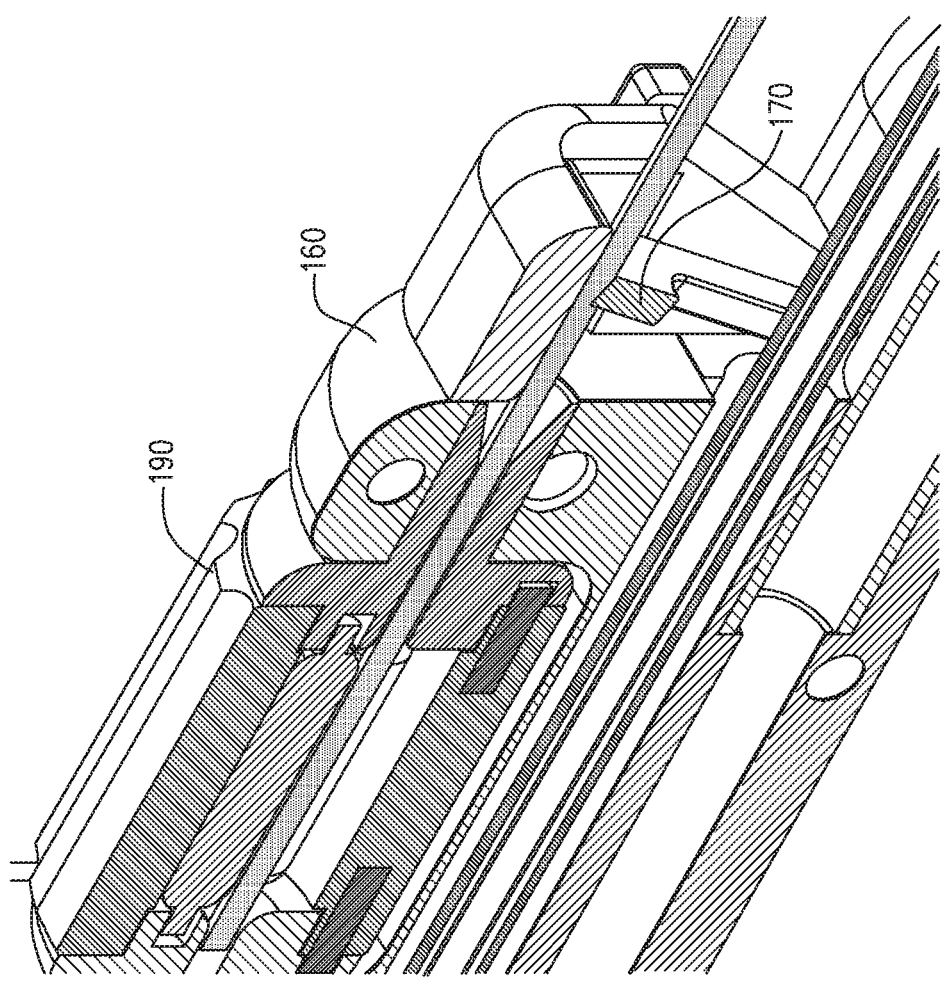

FIG. 5 is a schematic diagram of a distal tip 122 of articulated section 84, according to an embodiment of the present invention. Tip 122 comprises a camera 124, and illumination channels 126 providing light for the camera. Channels 126 may use optic fibers, receiving their light from a white light LED 130 proximal to the camera. Alternatively or additionally, the light from the channels may be provided from the LED by reflection and diffusion from a cavity containing the LED.

The front surface of the camera and the illumination channels may be cleaned by injecting fluid through fluid channels 134. The fluid is deflected by deflectors 138 so that it traverses the faces of the camera and the illumination channels. The cleaning fluid is typically conveyed to channels 134 through tubing (not shown in the figures) connected to the irrigation fluid channel described herein.

Distal tip 122 also comprises at least one magnetic sensor 32, which, as described above with reference to FIG. 1, allows the distal tip to be tracked using magnetic tracking system 23. Some embodiments of the invention comprise other magnetic sensors 32 that may be located in tube 100.

For clarity, cabling for the sensor, the camera and the LED are not shown in the figures. Also not shown in FIG. 5 for clarity, are guidewire 110 and mechanism 114, which during much of a procedure typically traverse distal tip 122. (They typically do not traverse the tip prior to their introduction into patient 22, and after removal from the patient.)

Returning to FIG. 2, proximal section 80 comprises a tool chassis 142, which includes a first channel or track 146 within which are located a guidewire and balloon insertion mechanism 150. At the base of first track 146 is a second channel or track 148, which permits the passage of the guidewire and of the balloon insertion mechanism from the proximal section to the distal section, as well as allowing the guidewire and the mechanism to move proximally and distally.

FIGS. 6-10 are schematic diagrams of guidewire and balloon insertion mechanism 150, according to an embodiment of the present invention. An adjusting device 160 of the mechanism runs proximally and distally in track 146 (FIG. 2) in tool chassis 142. Device 160 comprises an actuating gearwheel 164 and an intermediate gearwheel 166, the latter contacting guidewire 110 after the guidewire has been inserted into the device. Rotation of actuating gearwheel 164, typically by physician 54 pressing and pushing his/her thumb against the gearwheel, translates guidewire 110 in the same direction as the direction of the thumb movement. Release of the pressure on gearwheel 164 frees the guidewire from contact with intermediate gearwheel 166.

As stated above device 160 also travels in track 146, and at its distal side the device is connected to balloon sinuplasty mechanism 114 running in second track 148. Movement of device 160 forward or backward along track 146, typically by the physician using one of his/her fingers or thumb in an indentation 162 in the device, consequently translates sinuplasty mechanism 114 forward or backward. Any possible movement of the guidewire, while device 160 is moved, may be prevented by actuation of a guidewire locking lever 170 (FIG. 10), which locks the guidewire to tool chassis 142.

A rotatable mechanism 180 is located within a second, proximal, indentation 182 of first device 160. Mechanism 180 enables rotation of guidewire 110 about its axis of symmetry. Mechanism 180 comprises three cylindrical rollers 184 which have axes parallel to the guidewire axis, and which are symmetrically disposed in and contact a non-circular enclosure 186, typically an equilateral curvilinear triangle right prism enclosure formed within a rotatable knob 190 of mechanism 180. Enclosure 186 is configured so that when rollers 184 are at the apices of the enclosure, they do not contact guidewire 110, but that on rotation of knob 190 the rollers are pushed in so that they contact the guidewire. The contact remains as knob 190 is further rotated, so that the further rotation rotates the guidewire.

Figure 11:
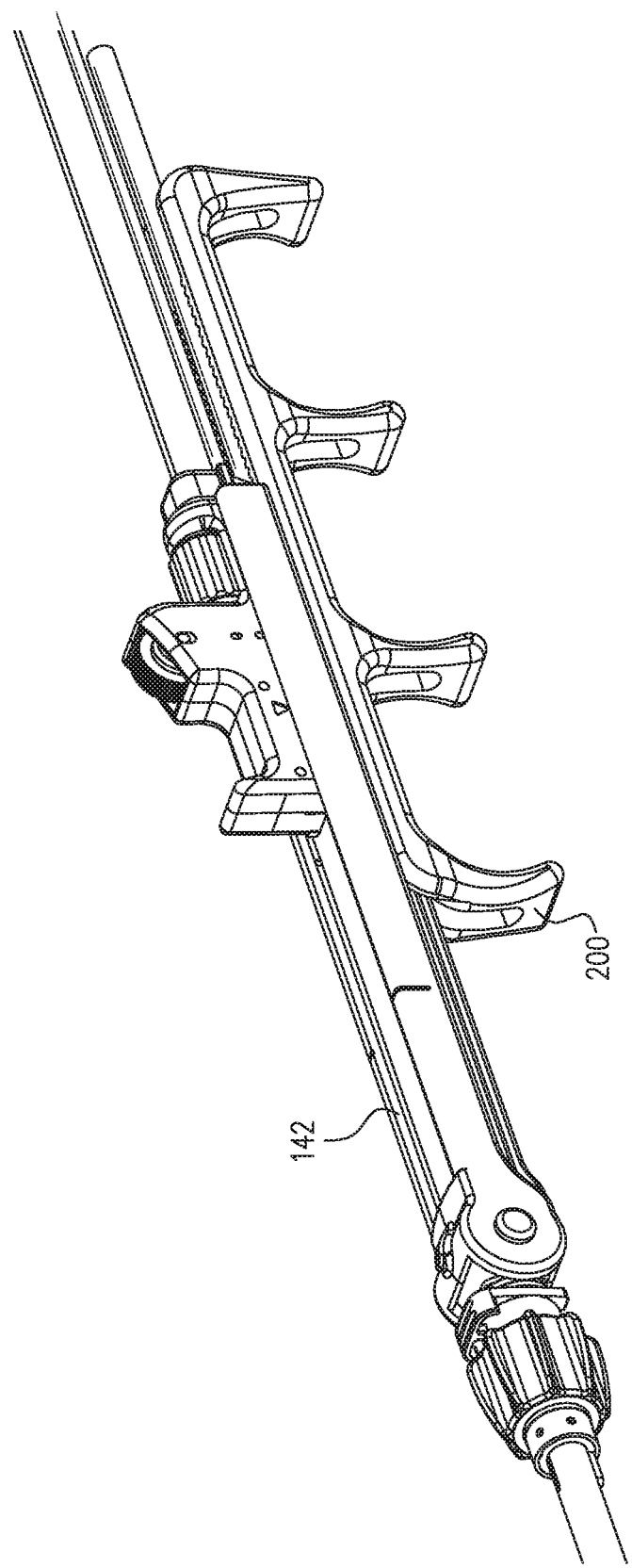
FIGS. 11 and 12 are schematic diagrams of a handle for a tool, according to an embodiment of the present invention.
Figure 12:
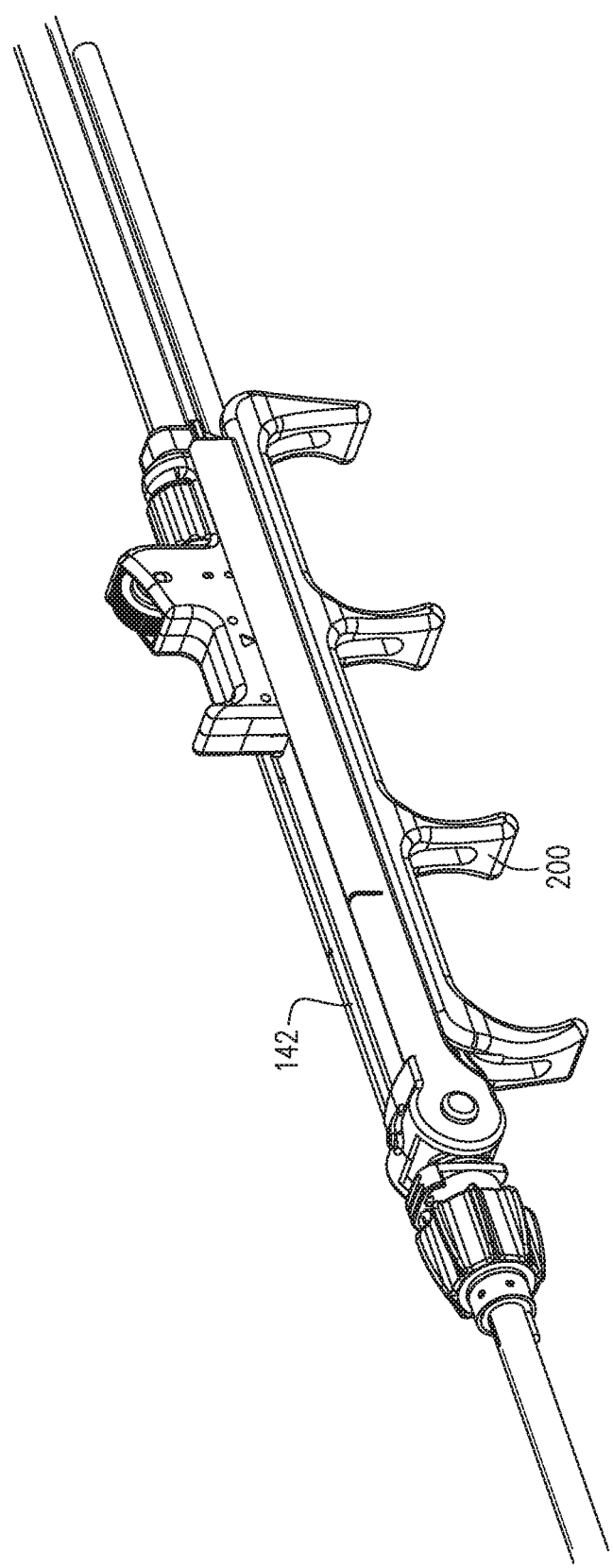
Figure 13:
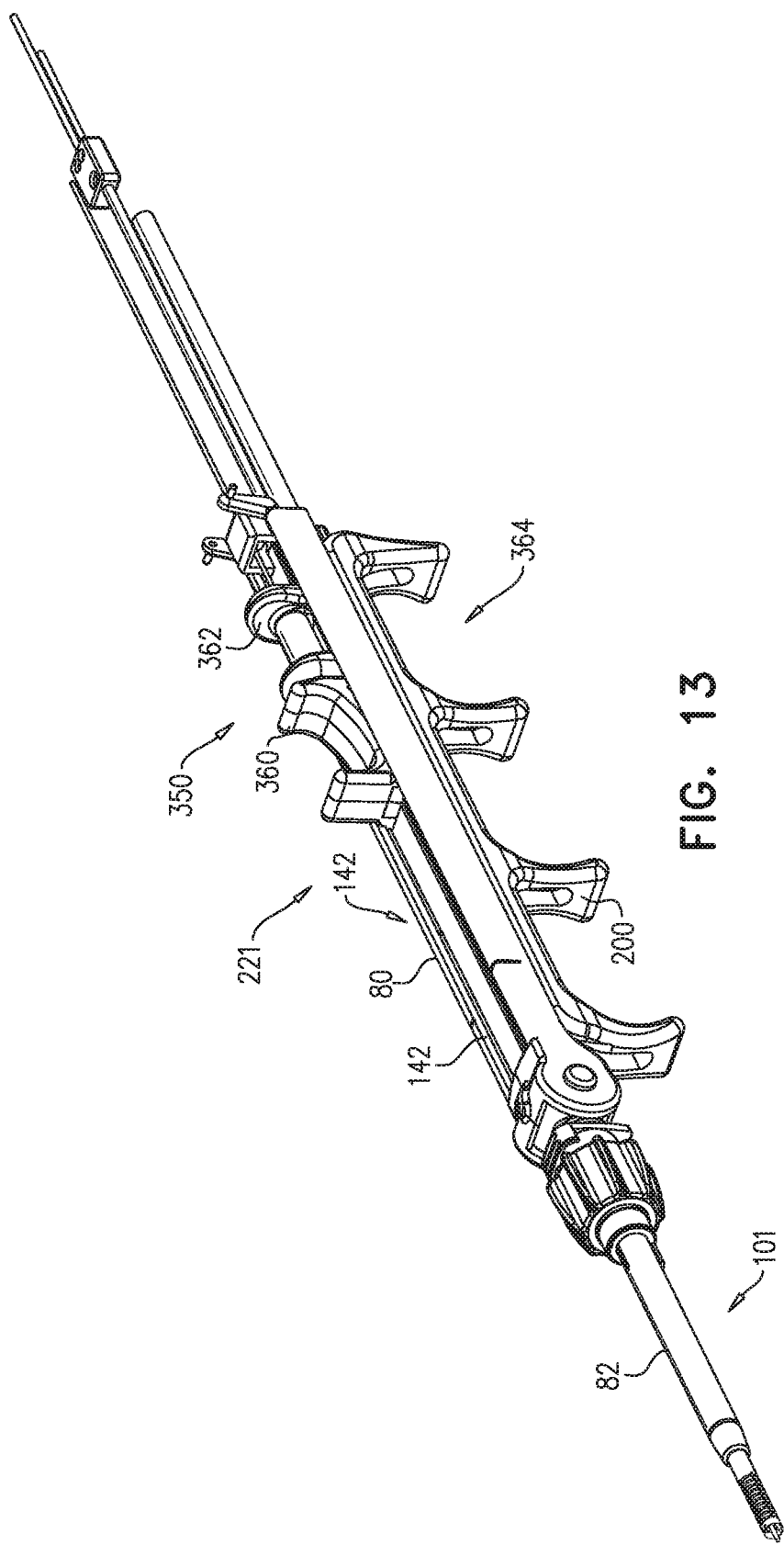
FIGS. 13-18 are schematic diagrams of a multifunctional ENT tool, according to an alternative embodiment of the present invention.
Figure 14:
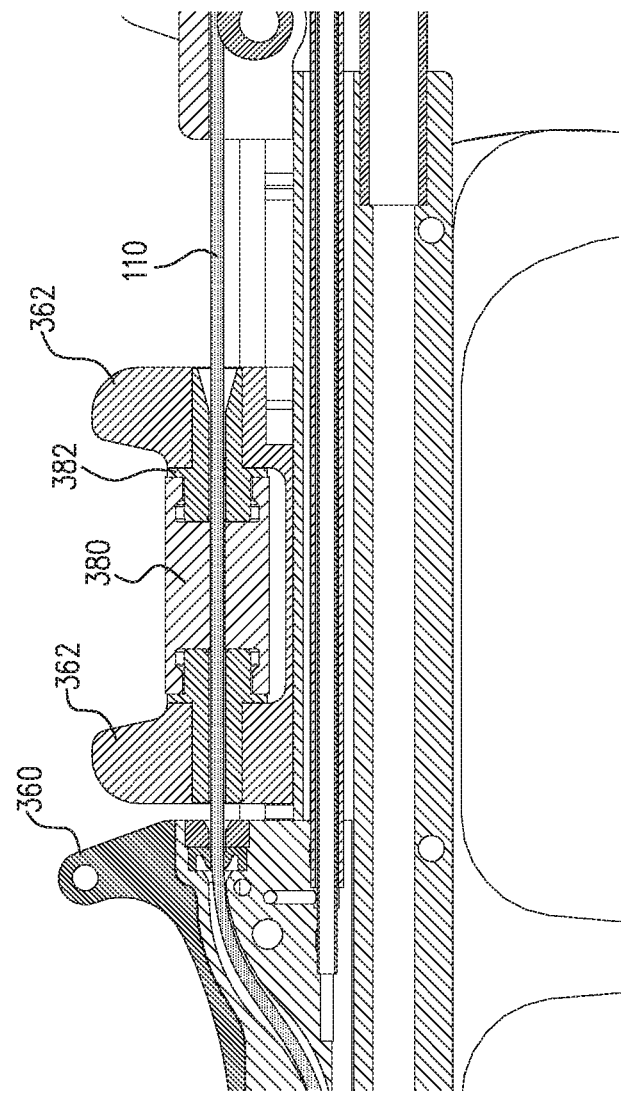
Figure 15:
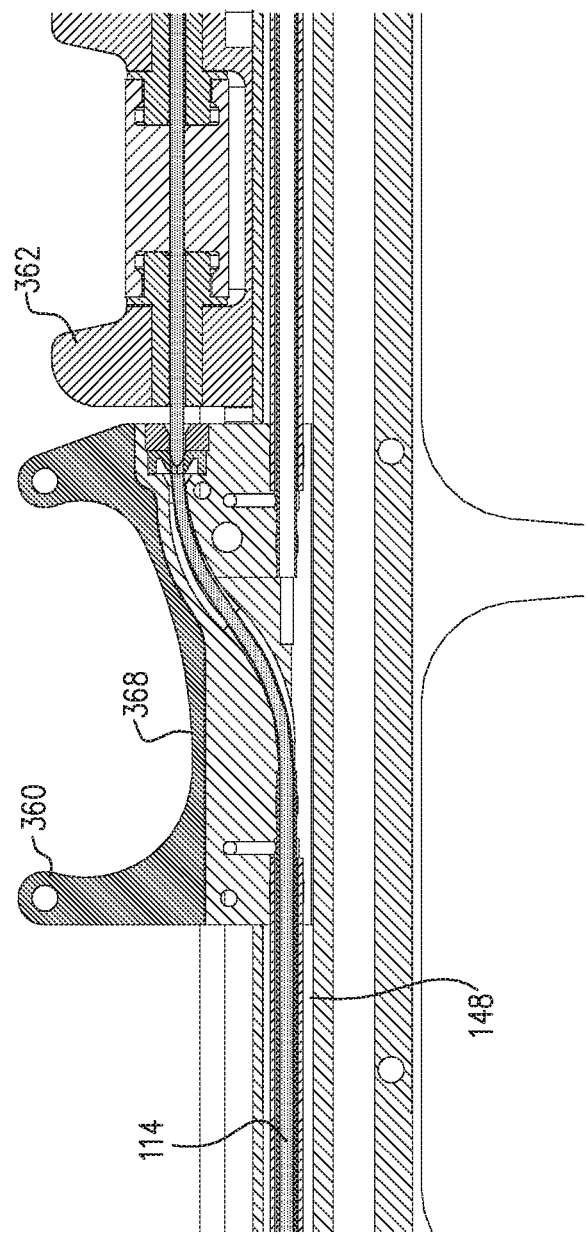
Figure 16:
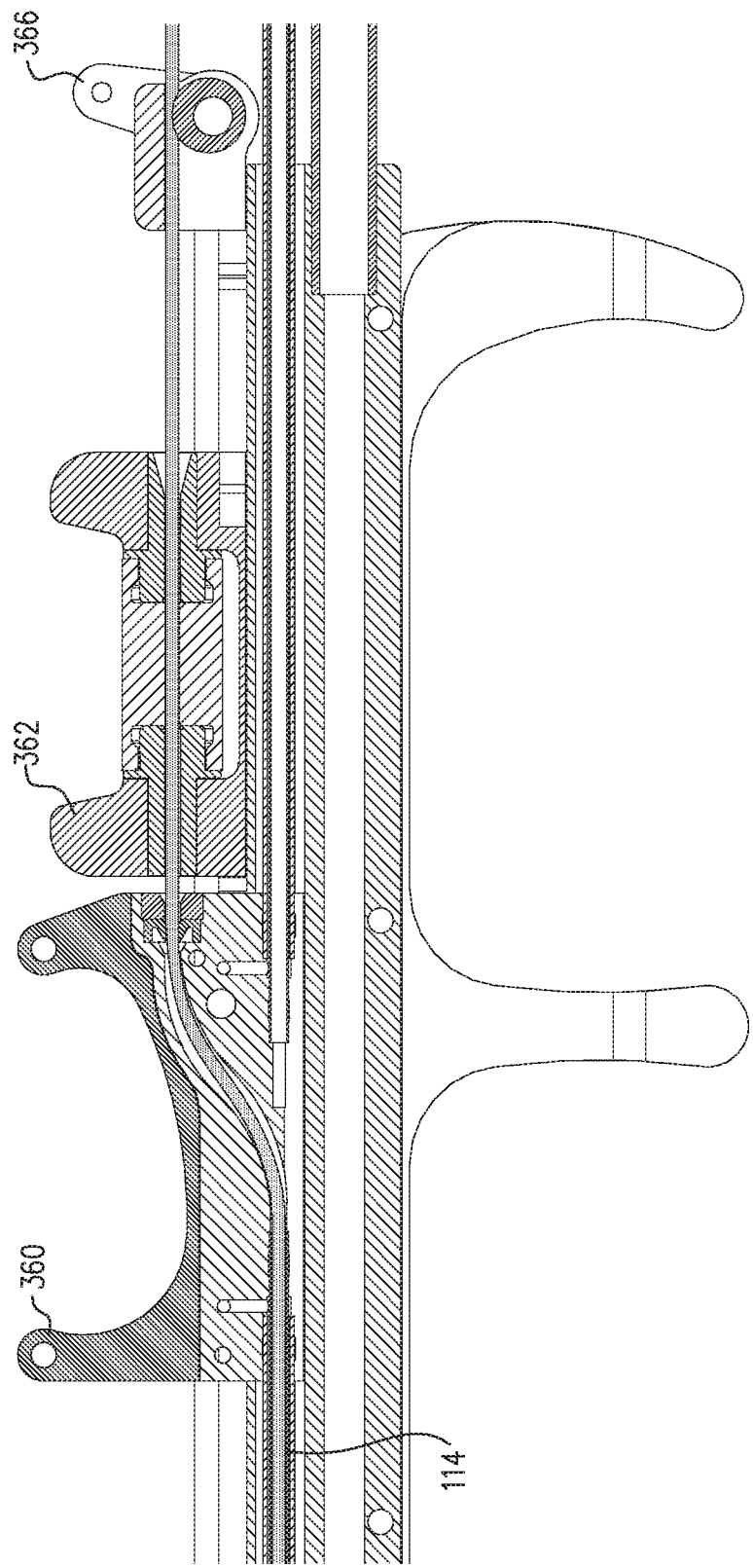
Figure 17:
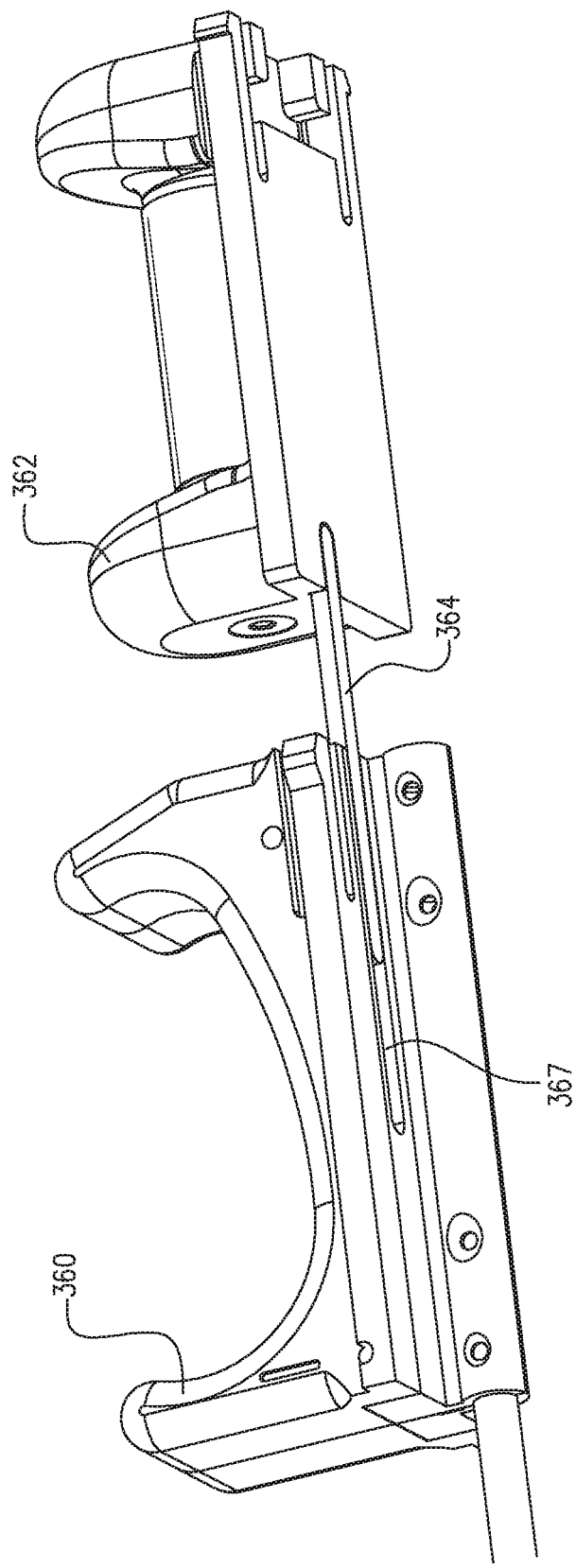
Figure 18:
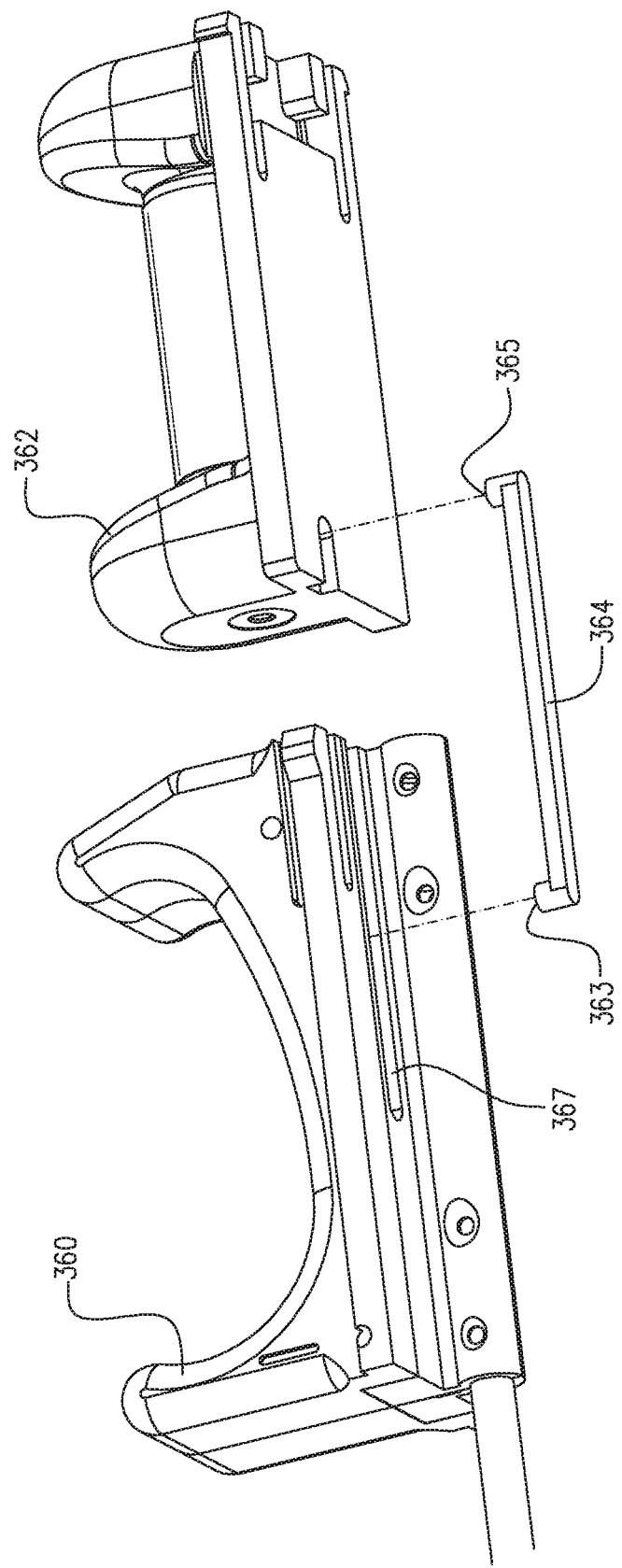
Figure 19:
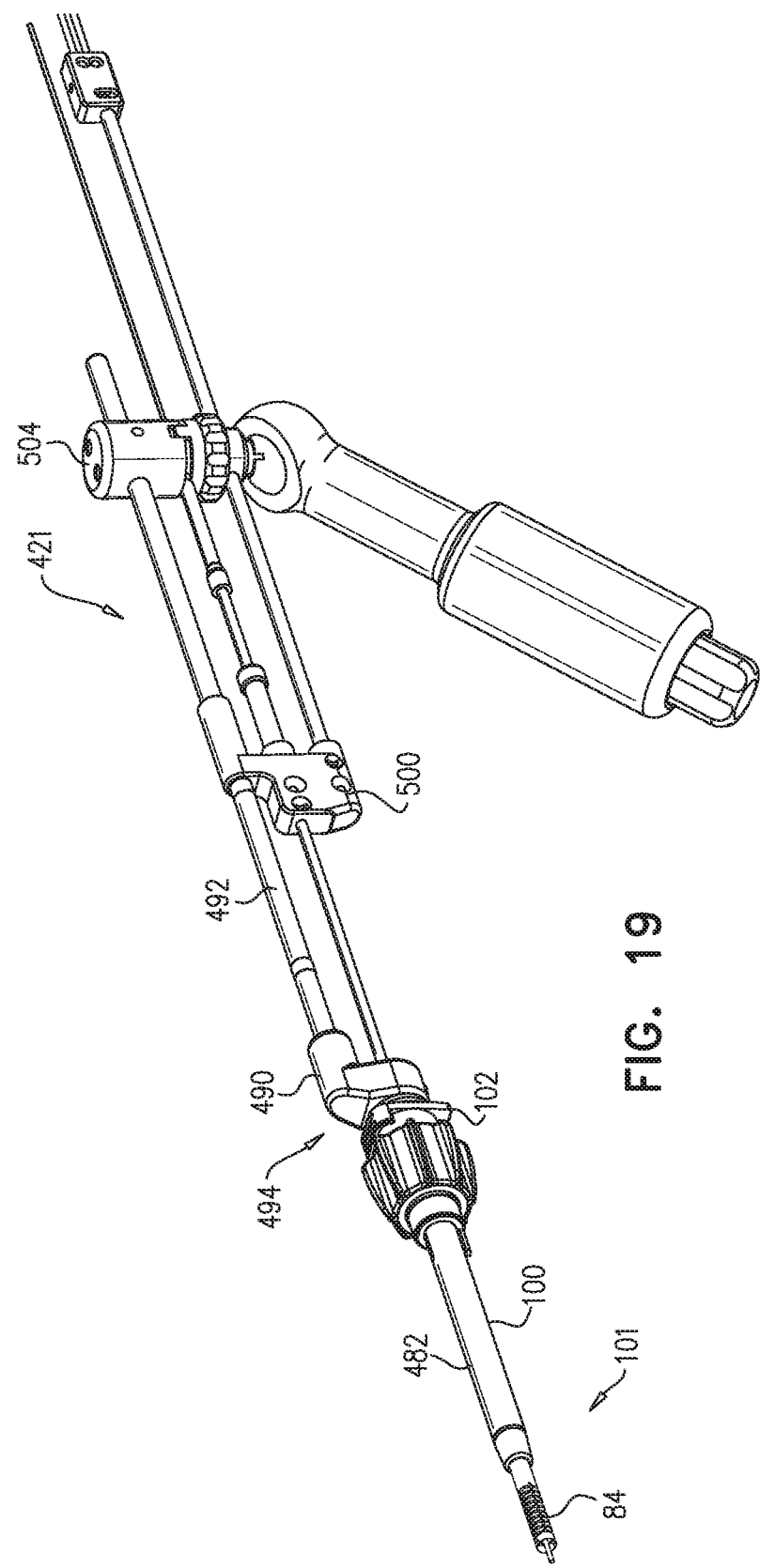

FIGS. 11 and 12 are schematic diagrams of a handle 200 for tool 21, according to an embodiment of the present invention. Handle 200 is connected to chassis 142, and is configured to slide adjustably with respect to the chassis. The figures show the handle in two different positions. Physician 54 may adjust the handle, by sliding and then fixating the handle, so that it is in a comfortable position for the physician.

FIGS. 13-18 are schematic diagrams of a multifunctional ENT tool 221, according to an alternative embodiment of the present invention. Apart from the differences described below, the operation of tool 221 is generally similar to that of tool 21 (FIGS. 1-12), and elements indicated by the same reference numerals in both tools 21 and 221 are generally similar in construction and in operation. Thus, apart from a change in mechanism 150 in proximal section 80, as described below, the remaining parts of the proximal section, distal section 82, tubular probe 101, and handle 200 are all substantially the same in the two tools.

In tool 221 mechanism 150 of tool 21 is replaced by a guidewire and balloon insertion mechanism 350 in tool 221. Mechanism 350 comprises two adjusting devices 360 and 362 which run proximally and distally in track 146 (FIG. 2) in tool chassis 142. Devices 360 and 362 are coupled together, in embodiments of the present invention, by a generally U-shaped couple 364 (FIGS. 13, 17, 18) having "arms" 363, 365. Arm 363 slides in a slot 367 in the base of device 360, so permitting the two devices 360, 362 to separate by a limited distance, defined by the distance between the "arms" of the U, the lengths of the two devices, and an available length of the slot.

Balloon sinuplasty mechanism 114 is connected to the distal side of device 360, and the mechanism slides in second track 148. Thus, movement of device 360 forward or backward along first track 146, typically by the physician using one of his/her fingers or thumb in an indentation 368 in the device, consequently translates sinuplasty mechanism 114 forward or backward. Typically, in order to prevent the guidewire moving when the sinuplasty mechanism is moved, the guidewire is locked to chassis 142 by a lever 366.

In contrast to the rotatable mechanism 180 of device 160, device 362 comprises a compression mechanism 380 located in an indentation 382 of the device. Mechanism 380 has a generally tubular structure having a central lumen permitting free passage of guidewire 110 through the lumen, and the compression mechanism is held within indentation 382 so that it is able to rotate about its central lumen. Compression mechanism 380 is formed from a rubber-like, typically silicone material, and is configured so that pressure from a thumb or finger from the physician deforms the mechanism so that it grips the guidewire.

Thus, by the physician applying pressure on mechanism 380 the physician is able to grip the guidewire, and while still applying the pressure, rotate the mechanism and the gripped guidewire. In addition, while gripping the guidewire, the physician is able to move the guidewire distally and proximally, relative to the sinuplasty mechanism, within the limits set by U-shaped couple 364.

FIGS. 19-23 are schematic diagrams of a multifunctional ENT tool 421, according to a further alternative embodiment of the present invention. While a distal section 482 of tool 421 is generally similar to section 82 of tools 21 and 221, it differs from the distal section of those tools by not being connected to the remaining elements of tool 421 by a joint. Thus in tool 421 articulated section 84 and tube 100 can respectively bend and rotate independently, according to the position of sliding control 102, but because there is no joint at its proximal end, the distal section cannot rotate around an axis orthogonal to the axis of symmetry of the tube.

Distal section 482 is removably coupled at its proximal end to an r-shaped connector 490, and the r-shaped connector is in turn fixedly connected to a suction tube 492. Connector 490 comprises a passage 494, which connects a central lumen of tube 492 to the lumen of tube 100. Thus, suction applied to the proximal end of suction tube 492 transfers to the lumen of tube 100.

Tube 492 acts as a retaining rail for other elements of tool 421, in particular for a balloon sinuplasty mechanism holder 500, and for a tool lock 504. Both holder 500 and lock 504 are able to slide along the rail until they are locked in position.

Balloon sinuplasty mechanism 114 is fixed to holder 500 by being inserted into a retaining hole 502 in the distal side of the holder (FIG. 23). Mechanism 114 comprises two concentric tubes, an inner tube 506 and an outer tube 508, with an air channel 510 between the tubes. Inner tube 506 is longer than outer tube 508, and a balloon 512 is connected between the distal ends of the two tubes, so as to seal the two ends. Passage of air into the air channel causes the balloon to inflate.

Holder 500 has a holder air channel 520 within the holder, and the holder air channel connects to air channel 510 of mechanism 114. Holder air channel 520 is connected at the proximal side of the holder to an inner tube 524, which is configured to feed air into air channels 520 and 510.

Holder 500 also has a holder water channel 530 within the holder, and the holder water channel connects to a channel 534 formed by a gap 540 between inner tube 506 of mechanism 114 and guidewire 110. Holder water channel 530 is connected at the proximal side of the holder to an outer tube 538, concentric with inner tube 524, and tube 538 is configured to feed water into the holder water channel and thus into gap 540.

As shown in the figures, guidewire 110 feeds through lock 504, and, via a tube 550 connected to the lock and a tube 554 connected to holder 500, the guidewire feeds into a central lumen of inner tube 506 of the balloon sinuplasty mechanism. There is flexible tubing 560 between tube 550 and tube 554, and the guidewire passes through a lumen of the tubing.

Lock 504, in an unlocked configuration allows tubes 524 and 538 to slide within the lock, so that the physician is able to move the tubes, and thus the connected holder 500 and balloon sinuplasty mechanism 114, distally and proximally. Also in the unlocked configuration guidewire 110 is free to move, and the physician may move the guidewire distally and proximally, as well as rotating the guidewire, by gripping flexible tubing 560.

Lock 504 comprises a rotatable knob 570, which rotates on a screw thread 572, and the knob is configured so that rotation of the knob transfers the lock from its unlocked configuration to a locked configuration. In the locked configuration the lock is fixedly connected to outer tube 538, guidewire 110, and suction tube 492.

It will be apparent that in the unlocked configuration of lock 504 both the guidewire and the sinuplasty mechanism are free to move, while in the locked configuration of the lock both the guidewire and the sinuplasty mechanism are fixed.

A handle 580 couples to lock 504 via a universal joint 582, and once physician 54 has determined a convenient position for the handle the universal joint may be locked by turning a locking knob 586.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An ear, nose, and throat (ENT) tool, comprising:
   (a) a tool chassis having a chassis channel and a tool chassis distal end;
   (b) a tubular probe dimensioned to be inserted into a passageway in an ear, a nose, or a throat of a human patient, the probe being rotatable about a probe axis of symmetry, and having a probe proximal end rotatingly connected to the tool chassis distal end;
   (c) a balloon insertion mechanism, slidingly located within the chassis channel, configured to fixedly accept a balloon sinuplasty mechanism inserted within the tubular probe;
   (d) a guidewire adjustment section fixedly attached to the balloon insertion mechanism, the section having a rotatable enclosure having an interior cavity; and
   (e) a plurality of rollers disposed within the interior cavity of the enclosure, wherein each roller includes an exterior surface, wherein the interior cavity of the enclosure is configured to engage the exterior surface of each roller upon rotation of the enclosure relative to the rollers and thereby cause movement of the rollers toward the guidewire on rotation of the enclosure, wherein the plurality of rollers is configured to grip and rotate a guidewire positioned between the rollers on rotation of the enclosure, and absent rotation of the enclosure, the plurality of rollers are configured to release the guidewire and permit distal and proximal translation of the guidewire.

2. The tool according to claim 1, wherein the tool chassis distal end comprises a joint connected to the probe proximal end, wherein the joint is configured to enable rotation of the tubular probe about an axis orthogonal to the probe axis of symmetry.

3. The tool according to claim 1, wherein the balloon insertion mechanism comprises one or more gearwheels configured to engage the guidewire on application of pressure to the one or more gearwheels, and to disengage the guidewire on removal of the pressure, and configured, on application of the pressure, to translate the guidewire distally and proximally on rotation of the one or more gearwheels.

4. The tool according to claim 1, wherein the rotatable enclosure comprises an equilateral curvilinear triangular right prism, and wherein the plurality of rollers comprises three rollers disposed within the equilateral curvilinear triangular right prism.

5. The tool according to claim 1, and comprising a camera fixedly installed in a distal tip of the tubular probe.

6. The tool according to claim 5, and comprising one or more illumination channels in the distal tip configured to provide light for the camera.

7. The tool according to claim 6, and comprising, in the distal tip, one or more fluid channels and deflectors configured to convey fluid that traverses faces of the camera and the illumination channels.

8. A method, comprising:
(a) providing an ENT (ear, nose, and throat) tool chassis having a chassis channel and a tool chassis distal end;
(b) dimensioning a tubular probe, having a probe proximal end, to be inserted into a passageway of an ear, a nose, or a throat of a human patient, the probe being rotatable about a probe axis of symmetry;
(c) rotatingly connecting the probe proximal end to the tool chassis distal end;
(d) slidingly locating a balloon insertion mechanism within the chassis channel;
(e) configuring the balloon insertion mechanism to fixedly accept a balloon sinuplasty mechanism penetrating the tubular probe;
(f) fixedly attaching a guidewire adjustment section to the balloon insertion mechanism, the section having a rotatable enclosure;
(g) disposing a plurality of rollers within an interior cavity of the enclosure; and
(h) configuring the rollers so that, on rotation of the enclosure, the interior cavity directly bears against the rollers, thereby gripping and rotating a guidewire positioned between the rollers, and absent rotation of the enclosure, release the guidewire and permit distal and proximal translation of the guidewire.

9. The method according to claim 8, wherein the tool chassis distal end comprises a joint connected to the probe proximal end, wherein the joint is configured to enable rotation of the tubular probe about an axis orthogonal to the probe axis of symmetry.

10. The method according to claim 8, wherein the balloon insertion mechanism comprises one or more gearwheels configured to engage the guidewire on application of pressure to the one or more gearwheels, and to disengage the guidewire on removal of the pressure, and configured, on application of the pressure, to translate the guidewire distally and proximally on rotation of the one or more gearwheels.

11. The method according to claim 8, wherein the rotatable enclosure comprises an equilateral curvilinear triangular right prism enclosure, and wherein the plurality of rollers comprises three rollers disposed within the enclosure.

12. The method according to claim 8, further comprising fixedly installing a camera in a distal tip of the tubular probe.

13. The method according to claim 12, further comprising providing one or more illumination channels in the distal tip so as to provide light for the camera.

14. The method according to claim 13, further comprising positioning in the distal tip one or more fluid channels and deflectors configured to convey fluid that traverses faces of the camera and the illumination channels.

15. The method according to claim 8, further comprising configuring the rollers so that, on rotation of the rotatable enclosure, the rollers move inwardly to grip and rotate a guidewire positioned between the rollers.

16. An ear, nose, and throat (ENT) tool, comprising:
(a) a tool chassis having a chassis channel and a tool chassis distal end;
(b) a tubular probe dimensioned to be inserted into a passageway in an ear, a nose, or a throat of a human patient, the tubular probe being rotatable about a probe axis of symmetry, and having a probe proximal end rotatingly connected to the tool chassis distal end, wherein tool chassis distal end includes a joint connected to the tubular probe proximal end, wherein the joint is configured to enable rotation of the tubular probe about an axis orthogonal to the probe axis of symmetry;
(c) a balloon insertion mechanism, slidingly located within the chassis channel, configured to fixedly accept a balloon sinuplasty mechanism inserted within the tubular probe;
(d) a guidewire adjustment section fixedly attached to the balloon insertion mechanism, the guidewire adjustment section having a rotatable enclosure; and
(e) a plurality of rollers, wherein each of the plurality of rollers includes an outermost surface, wherein the plurality of rollers is disposed within the rotatable enclosure and configured so that on rotation of the rotatable enclosure the enclosure engages the outermost surface of the rollers and the outermost surface of the rollers grips and rotates a guidewire positioned between the rollers, and, absent rotation of the rotatable enclosure, release the guidewire and permit distal and proximal translation of the guidewire.

17. The tool according to claim 1, wherein the rollers are configured to move inwardly to grip and rotate guidewire upon rotation of the rotatable enclosure.

18. The tool according to claim 1, wherein each roller of the plurality of rollers includes an axis that is parallel to the guidewire.

19. The tool according to claim 1, wherein the plurality of rollers is symmetrically disposed within a non-circular portion of enclosure.

20. The tool according to claim 1, wherein the rotatable enclosure includes a plurality of apexes positioned within the rotatable enclosure, wherein the rotatable enclosure is configured to allow each roller to remain in a respective apex, absent rotation of the rotatable enclosure.

\* \* \* \* \*